United States Patent
Okamoto et al.

(10) Patent No.: US 7,230,079 B2
(45) Date of Patent: Jun. 12, 2007

(54) ANTIALLERGIC AGENT

(75) Inventors: Iwao Okamoto, Okayama (JP); Norie Arai, Okayama (JP); Keizo Kohno, Okayama (JP); Masashi Kurimoto, Okayama (JP); Osamu Sano, Okayama (JP)

(73) Assignee: Ken Hayashibara, Okayama (JP)

( * ) Notice: Subject to any disclaimer, the term of this patent is extended or adjusted under 35 U.S.C. 154(b) by 26 days.

(21) Appl. No.: 10/525,567

(22) PCT Filed: Aug. 26, 2003

(86) PCT No.: PCT/JP03/10795

§ 371 (c)(1), (2), (4) Date: Feb. 25, 2005

(87) PCT Pub. No.: WO2004/019971

PCT Pub. Date: Mar. 11, 2004

(65) Prior Publication Data

US 2006/0134127 A1 Jun. 22, 2006

(30) Foreign Application Priority Data

Aug. 29, 2002 (JP) ............................. 2002-252087

(51) Int. Cl.
*C07K 1/00* (2006.01)
(52) U.S. Cl. ............................................ 530/350
(58) Field of Classification Search ............... 530/350; 514/12
See application file for complete search history.

(56) References Cited

U.S. PATENT DOCUMENTS 6,165,982 A * 12/2000 Yamada et al. ............... 514/21

FOREIGN PATENT DOCUMENTS

JP 100236/97 4/1997

OTHER PUBLICATIONS

Albert et al., Journal of Apicultural Research, 1996, 35(2), p. 63-68.*
Ohashi et al., Eur. J. Biochem., 1997, 249, p. 797-802.*
Klaudiny et al., Journal of Apicultural Research, 1994, 33(2), p. 105-111.*
Malecova et al., Gene, 2003, 303, p. 165-175.*
Artcle: Royal Jelly Proteins as aTool for Development of Functional Ingredeints for Health, Standing Commission of Apitherapy, pp. 1-5.*
Article: Benefits of Royal Jelly, updated on Feb. 16, 2006, pp. 1-3.*
Schmitzova J et al "A family of major royal jelly proteins of the honeybee Apis Mellifera L." Cellular and Molecular Life Sciences, (1998) vol. 54, pp. 1020-1030.
Hideki Oka et al "Th Saibo Otosei no Chosetsu o Kaishita, Royal jelly no Allergy Han'no Yokusei Sayo", Biotherapy (Tokyo), (2000) vol. 14, No. 2, pp. 145-150.
Mari Kataoka et al "Royal jelly no Ko-Allergy Sayo no Kento" Nat. Med., (2001), vol. 55, No. 4, pp. 174-180.
Oka H et al "Suppression of allergic reactions by royal jelly in association with the restoration of macrophage function and the improvement of Th1/Th2 cell responses", Int. Immunopharmacol., (2001), pp. 521-532.
Alberts S et al "Molecular characterization of MRJP3, highly polymorphic protein of honeybee (Apis Mellifera) royal jelly", Insect Biochem. Mol. Biol., (1999) pp. 427-434.

* cited by examiner

*Primary Examiner*—Karen Cochrane Carlson
*Assistant Examiner*—Agnes B. Rooke
(74) *Attorney, Agent, or Firm*—Browdy and Neimark, PLLC

(57) ABSTRACT

It is intended to provide an anti-allergic agent, which efficaciously relieves symptoms accompanying an allergic disease without causing any serious side effect. This object is achieved by providing an anti-allergic agent which contains, as an effective ingredient, proteins collected from royal jelly or purified royal jelly, or royal jelly or purified royal jelly containing the proteins.

5 Claims, 5 Drawing Sheets

SEQUENCE LISTING

<160> NUMBER OF SEQ ID NOS: 12

<210> SEQ ID NO 1
<211> LENGTH: 10
<212> TYPE: PRT
<213> ORGANISM: Apis mellifera

<400> SEQUENCE: 1

Ala Ala Val Asn His Gln Arg Lys Ser Ala
1               5                   10

<210> SEQ ID NO 2
<211> LENGTH: 25
<212> TYPE: PRT
<213> ORGANISM: Apis mellifera

<400> SEQUENCE: 2

Asn Ile Leu Arg Gly Glu Ser Leu Asn Lys Ser Leu Pro Ile Leu His
1               5                   10                  15

Glu Trp Lys Phe Phe Asp Tyr Asp Phe
            20                  25

<210> SEQ ID NO 3
<211> LENGTH: 524
<212> TYPE: PRT
<213> ORGANISM: Apis mellifera

<400> SEQUENCE: 3

Ala Ala Val Asn His Gln Arg Lys Ser Ala Asn Asn Leu Ala His Ser
1               5                   10                  15

Met Lys Val Ile Tyr Glu Trp Lys His Ile Asp Phe Asp Phe Gly Ser
            20                  25                  30

Asp Glu Arg Arg Asp Ala Ala Ile Lys Ser Gly Glu Phe Asp His Thr
        35                  40                  45

Lys Asn Tyr Pro Phe Asp Val Asp Arg Trp Arg Asp Lys Thr Phe Val
    50                  55                  60

Thr Ile Glu Arg Asn Asn Gly Val Pro Ser Ser Leu Asn Val Val Thr
65                  70                  75                  80

Asn Lys Lys Gly Lys Gly Gly Pro Leu Leu Arg Pro Tyr Pro Asp Trp
                85                  90                  95

Ser Phe Ala Lys Tyr Glu Asp Cys Ser Gly Ile Val Ser Ala Phe Lys
            100                 105                 110

Ile Ala Val Asp Lys Phe Asp Arg Leu Trp Val Leu Asp Ser Gly Leu
        115                 120                 125

Val Asn Asn Gln Pro Met Cys Ser Pro Lys Leu Leu Thr Phe Asp
    130                 135                 140

Leu Lys Thr Ser Lys Leu Val Lys Gln Val Glu Ile Pro His Asn Ile
145                 150                 155                 160

Ala Val Asn Ala Thr Thr Gly Met Gly Glu Leu Val Ser Leu Ala Val
                165                 170                 175

Gln Ala Ile Asp Arg Thr Asn Thr Met Val Tyr Ile Ala Asp Glu Lys
            180                 185                 190

Gly Glu Gly Leu Ile Met Tyr Gln Asn Ser Asp Asp Ser Phe His Arg
        195                 200                 205

-continued

```
Leu Thr Ser Asn Thr Phe Asp Tyr Asp Pro Arg Tyr Thr Lys Leu Thr
        210                 215                 220

Val Ala Gly Glu Ser Phe Thr Val Lys Asn Gly Ile Cys Gly Ile Ala
225                 230                 235                 240

Leu Ser Pro Val Thr Asn Asn Leu Tyr Tyr Ser Pro Leu Ser Ser His
                    245                 250                 255

Gly Leu Tyr Tyr Val Asp Thr Glu Gln Phe Arg Asn Pro Gln Tyr Glu
                260                 265                 270

Glu Asn Asn Val Gln Tyr Glu Gly Ser Gln Asp Ile Leu Asn Thr Gln
            275                 280                 285

Ser Phe Gly Lys Val Val Ser Lys Asn Gly Val Leu Phe Leu Gly Leu
        290                 295                 300

Val Gly Asn Ser Gly Ile Ala Cys Val Asn Glu His Gln Val Leu Gln
305                 310                 315                 320

Arg Glu Ser Phe Asp Val Val Ala Gln Asn Glu Glu Thr Leu Gln Met
                    325                 330                 335

Ile Val Ser Met Lys Ile Met Glu Asn Leu Pro Gln Ser Gly Arg Ile
                340                 345                 350

Asn Asp Pro Glu Gly Asn Glu Tyr Met Leu Ala Leu Ser Asn Arg Met
            355                 360                 365

Gln Lys Ile Ile Asn Asn Asp Phe Asn Phe Asn Asp Val Asn Phe Arg
        370                 375                 380

Ile Leu Gly Ala Asn Val Asp Asp Leu Met Arg Asn Thr Arg Cys Gly
385                 390                 395                 400

Arg Tyr His Asn Gln Asn Ala Gly Asn Gln Asn Ala Asp Asn Gln Asn
                    405                 410                 415

Ala Asp Asn Gln Asn Ala Asn Asn Gln Asn Ala Asp Asn Gln Asn Ala
                420                 425                 430

Asn Lys Gln Asn Gly Asn Arg Gln Asn Asp Asn Arg Gln Asn Asp Asn
            435                 440                 445

Lys Gln Asn Gly Asn Arg Gln Asn Asp Asn Lys Gln Asn Gly Asn Arg
450                 455                 460

Gln Asn Asp Asn Lys Gln Asn Gly Asn Arg Gln Asn Gly Asn Lys Gln
465                 470                 475                 480

Asn Asp Asn Lys Gln Asn Gly Asn Arg Gln Asn Asp Asn Lys Arg Asn
                    485                 490                 495

Gly Asn Arg Gln Asn Asp Asn Gln Asn Asn Gln Asn Asp Asn Asn Arg
                500                 505                 510

Asn Asp Asn Gln Val His His Ser Ser Lys Leu His
            515                 520
```

<210> SEQ ID NO 4
<211> LENGTH: 413
<212> TYPE: PRT
<213> ORGANISM: Apis mellifera
<220> FEATURE:
<221> NAME/KEY: misc_feature
<222> LOCATION: (344)..(344)
<223> OTHER INFORMATION: Xaa can be any naturally occurring amino acid

<400> SEQUENCE: 4

```
Asn Ile Leu Arg Gly Glu Ser Leu Asn Lys Ser Leu Pro Ile Leu His
1               5                   10                  15

Glu Trp Lys Phe Phe Asp Tyr Asp Phe Gly Ser Asp Glu Arg Arg Gln
            20                  25                  30
```

```
Asp Ala Ile Leu Ser Gly Glu Tyr Asp Tyr Lys Asn Asn Tyr Pro Ser
            35                  40                  45

Asp Ile Asp Gln Trp His Asp Lys Ile Phe Val Thr Met Leu Arg Tyr
    50                  55                  60

Asn Gly Val Pro Ser Ser Leu Asn Val Ile Ser Lys Lys Val Gly Asp
65                  70                  75                  80

Gly Gly Pro Leu Leu Gln Pro Tyr Pro Asp Trp Ser Phe Ala Lys Tyr
                85                  90                  95

Asp Asp Cys Ser Gly Ile Val Ser Ala Ser Lys Leu Ala Ile Asp Lys
            100                 105                 110

Cys Asp Arg Leu Trp Val Leu Asp Ser Gly Leu Val Asn Asn Thr Gln
        115                 120                 125

Pro Met Cys Ser Pro Lys Leu Leu Thr Phe Asp Leu Thr Thr Ser Gln
    130                 135                 140

Leu Leu Lys Gln Val Glu Ile Pro His Asp Val Ala Val Asn Ala Thr
145                 150                 155                 160

Thr Gly Lys Gly Arg Leu Ser Ser Leu Ala Val Gln Ser Leu Asp Cys
                165                 170                 175

Asn Thr Asn Ser Asp Thr Met Val Tyr Ile Ala Asp Glu Lys Gly Glu
            180                 185                 190

Gly Leu Ile Val Tyr His Asn Ser Asp Asp Ser Phe His Arg Leu Thr
        195                 200                 205

Ser Asn Thr Phe Asp Tyr Asp Pro Lys Phe Thr Lys Met Thr Ile Asp
    210                 215                 220

Gly Glu Ser Tyr Thr Ala Gln Asp Gly Ile Ser Gly Met Ala Leu Ser
225                 230                 235                 240

Pro Met Thr Asn Asn Leu Tyr Tyr Ser Pro Val Ala Ser Thr Ser Leu
                245                 250                 255

Tyr Tyr Val Asn Thr Glu Gln Phe Arg Thr Ser Asp Tyr Gln Gln Asn
            260                 265                 270

Asp Ile His Tyr Glu Gly Val Gln Asn Ile Leu Asp Thr Gln Ser Ser
        275                 280                 285

Ala Lys Val Val Ser Lys Ser Gly Val Leu Phe Phe Gly Leu Val Gly
    290                 295                 300

Asp Ser Ala Leu Gly Cys Trp Asn Glu His Arg Thr Leu Glu Arg His
305                 310                 315                 320

Asn Ile Arg Thr Val Ala Gln Ser Asp Glu Thr Leu Gln Met Ile Ala
                325                 330                 335

Ser Met Lys Ile Lys Glu Ala Xaa Pro His Val Pro Ile Phe Asp Arg
            340                 345                 350

Tyr Ile Asn Arg Glu Tyr Ile Leu Val Leu Ser Asn Lys Met Gln Lys
        355                 360                 365

Met Val Asn Asn Asp Phe Asn Phe Asp Val Asn Phe Arg Ile Met
    370                 375                 380

Asn Ala Asn Val Asn Glu Leu Ile Leu Asn Thr Arg Cys Glu Asn Pro
385                 390                 395                 400

Asp Asn Asp Arg Thr Pro Phe Lys Ile Ser Ile His Leu
                405                 410

<210> SEQ ID NO 5
<211> LENGTH: 1635
<212> TYPE: DNA
<213> ORGANISM: Apis mellifera
<220> FEATURE:
<221> NAME/KEY: CDS
```

<222> LOCATION: (1)..(1632)
<220> FEATURE:
<221> NAME/KEY: mat_peptide
<222> LOCATION: (61)..(1635)

<400> SEQUENCE: 5

| | | | | | | | | | | | | | | | | |
|---|---|---|---|---|---|---|---|---|---|---|---|---|---|---|---|---|
| atg | aca | aag | tgg | ttg | ttg | ctg | gtg | gtg | tgc | ctt | ggt | ata | gct | tgt | caa | 48 |
| Met | Thr | Lys | Trp | Leu | Leu | Leu | Val | Val | Cys | Leu | Gly | Ile | Ala | Cys | Gln | |
| -20 | | | | -15 | | | | -10 | | | | | -5 | | | |

| gat | gta | aca | agc | gca | gct | gtg | aat | cat | caa | aga | aaa | tct | gca | aat | aat | 96 |
|---|---|---|---|---|---|---|---|---|---|---|---|---|---|---|---|---|
| Asp | Val | Thr | Ser | Ala | Ala | Val | Asn | His | Gln | Arg | Lys | Ser | Ala | Asn | Asn | |
| | | -1 | 1 | | | | | 5 | | | | | 10 | | | |

| ttg | gca | cat | tct | atg | aaa | gtg | atc | tac | gaa | tgg | aaa | cac | att | gat | ttt | 144 |
|---|---|---|---|---|---|---|---|---|---|---|---|---|---|---|---|---|
| Leu | Ala | His | Ser | Met | Lys | Val | Ile | Tyr | Glu | Trp | Lys | His | Ile | Asp | Phe | |
| | | 15 | | | | 20 | | | | | 25 | | | | | |

| gat | ttc | ggt | agc | gat | gaa | aga | aga | gat | gct | gcg | att | aaa | tct | ggc | gaa | 192 |
|---|---|---|---|---|---|---|---|---|---|---|---|---|---|---|---|---|
| Asp | Phe | Gly | Ser | Asp | Glu | Arg | Arg | Asp | Ala | Ala | Ile | Lys | Ser | Gly | Glu | |
| | 30 | | | | | 35 | | | | | 40 | | | | | |

| ttt | gat | cac | aca | aaa | aat | tat | cct | ttc | gat | gtg | gac | aga | tgg | cgt | gat | 240 |
|---|---|---|---|---|---|---|---|---|---|---|---|---|---|---|---|---|
| Phe | Asp | His | Thr | Lys | Asn | Tyr | Pro | Phe | Asp | Val | Asp | Arg | Trp | Arg | Asp | |
| 45 | | | | | 50 | | | | | 55 | | | | | 60 | |

| aag | aca | ttt | gtc | acc | ata | gaa | agg | aac | aat | ggt | gta | cct | tct | tct | ttg | 288 |
|---|---|---|---|---|---|---|---|---|---|---|---|---|---|---|---|---|
| Lys | Thr | Phe | Val | Thr | Ile | Glu | Arg | Asn | Asn | Gly | Val | Pro | Ser | Ser | Leu | |
| | | | | 65 | | | | | 70 | | | | | 75 | | |

| aac | gtg | gta | act | aat | aaa | aag | ggc | aaa | ggt | gga | cct | ctt | cta | cga | cca | 336 |
|---|---|---|---|---|---|---|---|---|---|---|---|---|---|---|---|---|
| Asn | Val | Val | Thr | Asn | Lys | Lys | Gly | Lys | Gly | Gly | Pro | Leu | Leu | Arg | Pro | |
| | | | 80 | | | | | 85 | | | | | 90 | | | |

| tat | cct | gat | tgg | tcg | ttt | gcc | aaa | tac | gaa | gat | tgc | tct | gga | att | gtg | 384 |
|---|---|---|---|---|---|---|---|---|---|---|---|---|---|---|---|---|
| Tyr | Pro | Asp | Trp | Ser | Phe | Ala | Lys | Tyr | Glu | Asp | Cys | Ser | Gly | Ile | Val | |
| | 95 | | | | | 100 | | | | | 105 | | | | | |

| agc | gct | ttc | aaa | att | gcg | gtc | gac | aaa | ttt | gac | aga | tta | tgg | gtt | ctg | 432 |
|---|---|---|---|---|---|---|---|---|---|---|---|---|---|---|---|---|
| Ser | Ala | Phe | Lys | Ile | Ala | Val | Asp | Lys | Phe | Asp | Arg | Leu | Trp | Val | Leu | |
| 110 | | | | | 115 | | | | | 120 | | | | | | |

| gac | tca | ggt | ctt | gtc | aat | aat | aat | caa | cct | atg | tgc | tct | cca | aaa | ttg | 480 |
|---|---|---|---|---|---|---|---|---|---|---|---|---|---|---|---|---|
| Asp | Ser | Gly | Leu | Val | Asn | Asn | Asn | Gln | Pro | Met | Cys | Ser | Pro | Lys | Leu | |
| 125 | | | | | 130 | | | | | 135 | | | | | 140 | |

| tta | acc | ttt | gat | ctg | aaa | acc | tca | aaa | ttg | gtt | aag | caa | gtc | gag | ata | 528 |
|---|---|---|---|---|---|---|---|---|---|---|---|---|---|---|---|---|
| Leu | Thr | Phe | Asp | Leu | Lys | Thr | Ser | Lys | Leu | Val | Lys | Gln | Val | Glu | Ile | |
| | | | 145 | | | | | 150 | | | | | 155 | | | |

| cca | cat | aat | att | gcc | gta | aac | gcc | acc | aca | gga | atg | gga | gaa | tta | gtt | 576 |
|---|---|---|---|---|---|---|---|---|---|---|---|---|---|---|---|---|
| Pro | His | Asn | Ile | Ala | Val | Asn | Ala | Thr | Thr | Gly | Met | Gly | Glu | Leu | Val | |
| | | 160 | | | | | 165 | | | | | 170 | | | | |

| tca | cta | gct | gtt | caa | gct | ata | gat | cgt | acg | aat | act | atg | gtg | tac | ata | 624 |
|---|---|---|---|---|---|---|---|---|---|---|---|---|---|---|---|---|
| Ser | Leu | Ala | Val | Gln | Ala | Ile | Asp | Arg | Thr | Asn | Thr | Met | Val | Tyr | Ile | |
| | 175 | | | | | 180 | | | | | 185 | | | | | |

| gca | gac | gaa | aaa | ggc | gaa | ggt | tta | atc | atg | tat | caa | aac | tcc | gac | gat | 672 |
|---|---|---|---|---|---|---|---|---|---|---|---|---|---|---|---|---|
| Ala | Asp | Glu | Lys | Gly | Glu | Gly | Leu | Ile | Met | Tyr | Gln | Asn | Ser | Asp | Asp | |
| 190 | | | | | 195 | | | | | 200 | | | | | | |

| tcc | ttc | cat | cga | ttg | act | tcc | aat | act | ttc | gat | tac | gat | ccc | aga | tat | 720 |
|---|---|---|---|---|---|---|---|---|---|---|---|---|---|---|---|---|
| Ser | Phe | His | Arg | Leu | Thr | Ser | Asn | Thr | Phe | Asp | Tyr | Asp | Pro | Arg | Tyr | |
| 205 | | | | | 210 | | | | | 215 | | | | | 220 | |

| acc | aaa | ttg | aca | gtc | gct | gga | gaa | agt | ttc | aca | gtg | aaa | aat | gga | att | 768 |
|---|---|---|---|---|---|---|---|---|---|---|---|---|---|---|---|---|
| Thr | Lys | Leu | Thr | Val | Ala | Gly | Glu | Ser | Phe | Thr | Val | Lys | Asn | Gly | Ile | |
| | | | | 225 | | | | | 230 | | | | | 235 | | |

| tgt | gga | att | gca | ctt | agt | ccc | gtg | acg | aac | aat | ctt | tat | tac | agc | cct | 816 |
|---|---|---|---|---|---|---|---|---|---|---|---|---|---|---|---|---|
| Cys | Gly | Ile | Ala | Leu | Ser | Pro | Val | Thr | Asn | Asn | Leu | Tyr | Tyr | Ser | Pro | |
| | | | 240 | | | | | 245 | | | | | 250 | | | |

| ctc | tct | tct | cac | ggt | ttg | tat | tat | gtt | gat | acg | gaa | caa | ttc | agg | aat | 864 |
|---|---|---|---|---|---|---|---|---|---|---|---|---|---|---|---|---|
| Leu | Ser | Ser | His | Gly | Leu | Tyr | Tyr | Val | Asp | Thr | Glu | Gln | Phe | Arg | Asn | |
| | 255 | | | | | 260 | | | | | 265 | | | | | |

-continued

| | | |
|---|---|---|
| cca caa tat gaa gaa aat aac gtg caa tat gaa gga tct caa gat att<br>Pro Gln Tyr Glu Glu Asn Asn Val Gln Tyr Glu Gly Ser Gln Asp Ile<br>270                          275                          280 | | 912 |
| ttg aac act caa tca ttc ggt aaa gta gta tcg aaa aat ggc gtc ctt<br>Leu Asn Thr Gln Ser Phe Gly Lys Val Val Ser Lys Asn Gly Val Leu<br>285                          290                          295                        300 | | 960 |
| ttc ttg gga ctc gtg ggt aat tca ggt att gcc tgc gtg aat gaa cat<br>Phe Leu Gly Leu Val Gly Asn Ser Gly Ile Ala Cys Val Asn Glu His<br>                      305                          310                        315 | | 1008 |
| caa gta ctt cag aga gaa agt ttt gat gtt gtc gct cag aat gaa gag<br>Gln Val Leu Gln Arg Glu Ser Phe Asp Val Val Ala Gln Asn Glu Glu<br>                  320                          325                        330 | | 1056 |
| aca ctt caa atg atc gtt agt atg aaa atc atg gaa aat ctt cca caa<br>Thr Leu Gln Met Ile Val Ser Met Lys Ile Met Glu Asn Leu Pro Gln<br>335                          340                          345 | | 1104 |
| tcc ggc aga att aat gat cct gaa ggc aat gaa tat atg ttg gct ttg<br>Ser Gly Arg Ile Asn Asp Pro Glu Gly Asn Glu Tyr Met Leu Ala Leu<br>350                          355                          360 | | 1152 |
| agt aac aga atg caa aaa ata ata aac aat gat ttt aat ttc aac gac<br>Ser Asn Arg Met Gln Lys Ile Ile Asn Asn Asp Phe Asn Phe Asn Asp<br>365                          370                          375                        380 | | 1200 |
| gta aat ttc cga att ttg ggt gcg aat gta gat gac tta atg aga aac<br>Val Asn Phe Arg Ile Leu Gly Ala Asn Val Asp Asp Leu Met Arg Asn<br>                  385                          390                        395 | | 1248 |
| act cgt tgc gga aga tat cac aat cag aat gct ggc aat cag aat gct<br>Thr Arg Cys Gly Arg Tyr His Asn Gln Asn Ala Gly Asn Gln Asn Ala<br>                  400                          405                        410 | | 1296 |
| gac aat cag aat gct gac aat cag aat gct aac aat cag aat gct gat<br>Asp Asn Gln Asn Ala Asp Asn Gln Asn Ala Asn Asn Gln Asn Ala Asp<br>                      415                        420                        425 | | 1344 |
| aat cag aat gct aac aaa caa aat ggt aat aga caa aat gat aac aga<br>Asn Gln Asn Ala Asn Lys Gln Asn Gly Asn Arg Gln Asn Asp Asn Arg<br>430                          435                          440 | | 1392 |
| cag aat gat aac aag caa aat ggt aac aga cag aat gat aac aag caa<br>Gln Asn Asp Asn Lys Gln Asn Gly Asn Arg Gln Asn Asp Asn Lys Gln<br>445                          450                        455                        460 | | 1440 |
| aat ggt aac aga cag aat gat aac aag caa aat ggt aac aga caa aat<br>Asn Gly Asn Arg Gln Asn Asp Asn Lys Gln Asn Gly Asn Arg Gln Asn<br>                      465                          470                        475 | | 1488 |
| ggt aac aaa cag aat gat aac aag caa aat ggt aac aga cag aat gat<br>Gly Asn Lys Gln Asn Asp Asn Lys Gln Asn Gly Asn Arg Gln Asn Asp<br>                  480                          485                        490 | | 1536 |
| aac aag agg aat ggt aac agg caa aat gat aat caa aat aat cag aat<br>Asn Lys Arg Asn Gly Asn Arg Gln Asn Asp Asn Gln Asn Asn Gln Asn<br>                      495                          500                        505 | | 1584 |
| gat aat aat cga aat gat aat caa gtt cat cat tct tca aaa tta cat<br>Asp Asn Asn Arg Asn Asp Asn Gln Val His His Ser Ser Lys Leu His<br>510                          515                          520 | | 1632 |
| taa | | 1635 |

<210> SEQ ID NO 6
<211> LENGTH: 1245
<212> TYPE: DNA
<213> ORGANISM: Apis mellifera
<220> FEATURE:
<221> NAME/KEY: CDS
<222> LOCATION: (1)..(1242)
<220> FEATURE:
<221> NAME/KEY: mat_peptide
<222> LOCATION: (4)..(1242)

<400> SEQUENCE: 6

-continued

```
atg aac att ctt cga gga gag tct tta aac aaa tca tta ccc atc ctt      48
Met Asn Ile Leu Arg Gly Glu Ser Leu Asn Lys Ser Leu Pro Ile Leu
 -1   1               5                  10                  15 cac gaa tgg aaa ttc ttt gat tat gat ttc ggt agc gat gaa aga aga      96
His Glu Trp Lys Phe Phe Asp Tyr Asp Phe Gly Ser Asp Glu Arg Arg
                 20                  25                  30 caa gat gca att cta tct ggc gaa tac gac tac aag aat aat tat cca     144
Gln Asp Ala Ile Leu Ser Gly Glu Tyr Asp Tyr Lys Asn Asn Tyr Pro
             35                  40                  45 tcc gac att gac caa tgg cat gat aag att ttt gtc acc atg ctg aga     192
Ser Asp Ile Asp Gln Trp His Asp Lys Ile Phe Val Thr Met Leu Arg
         50                  55                  60 tac aat ggc gta cct tcc tct ttg aac gtg ata tct aaa aag gtc ggt     240
Tyr Asn Gly Val Pro Ser Ser Leu Asn Val Ile Ser Lys Lys Val Gly
     65                  70                  75 gat ggt ggt cct ctt cta caa cct tat ccc gat tgg tcg ttt gct aaa     288
Asp Gly Gly Pro Leu Leu Gln Pro Tyr Pro Asp Trp Ser Phe Ala Lys
 80                  85                  90                  95 tat gac gat tgc tct gga atc gtg agc gcc tca aaa ctt gcg atc gac     336
Tyr Asp Asp Cys Ser Gly Ile Val Ser Ala Ser Lys Leu Ala Ile Asp
                100                 105                 110 aaa tgc gac aga ttg tgg gtt ctg gac tca ggt ctt gtc aat aat act     384
Lys Cys Asp Arg Leu Trp Val Leu Asp Ser Gly Leu Val Asn Asn Thr
            115                 120                 125 caa ccc atg tgt tct cca aaa ctg ctc acc ttt gat ctg act acc tcg     432
Gln Pro Met Cys Ser Pro Lys Leu Leu Thr Phe Asp Leu Thr Thr Ser
        130                 135                 140 caa ttg ctc aag caa gtt gaa ata cca cat gat gtt gcc gta aat gcc     480
Gln Leu Leu Lys Gln Val Glu Ile Pro His Asp Val Ala Val Asn Ala
    145                 150                 155 act aca gga aag gga aga tta tca tct cta gct gtt caa tct tta gat     528
Thr Thr Gly Lys Gly Arg Leu Ser Ser Leu Ala Val Gln Ser Leu Asp
160                 165                 170                 175 tgc aat aca aat agc gat act atg gtg tac ata gca gac gag aaa ggt     576
Cys Asn Thr Asn Ser Asp Thr Met Val Tyr Ile Ala Asp Glu Lys Gly
                180                 185                 190 gaa ggt tta atc gtg tat cat aat tct gat gat tcc ttc cat cga ttg     624
Glu Gly Leu Ile Val Tyr His Asn Ser Asp Asp Ser Phe His Arg Leu
            195                 200                 205 act tcc aac act ttc gat tac gat cct aaa ttt acc aaa atg acg atc     672
Thr Ser Asn Thr Phe Asp Tyr Asp Pro Lys Phe Thr Lys Met Thr Ile
        210                 215                 220 gat gga gaa agt tac aca gcc caa gat gga att tct gga atg gct ctt     720
Asp Gly Glu Ser Tyr Thr Ala Gln Asp Gly Ile Ser Gly Met Ala Leu
    225                 230                 235 agt ccc atg act aac aat ctc tat tac agt cct gta gct tcc acc agt     768
Ser Pro Met Thr Asn Asn Leu Tyr Tyr Ser Pro Val Ala Ser Thr Ser
240                 245                 250                 255 ttg tat tat gtt aac acg gaa caa ttc aga aca tcc gat tat caa cag     816
Leu Tyr Tyr Val Asn Thr Glu Gln Phe Arg Thr Ser Asp Tyr Gln Gln
                260                 265                 270 aat gac ata cat tac gaa gga gtc caa aat att ttg gat acc caa tcg     864
Asn Asp Ile His Tyr Glu Gly Val Gln Asn Ile Leu Asp Thr Gln Ser
            275                 280                 285 tcc gct aaa gta gta tca aag agt ggc gtt ctc ttc ttc gga ttg gtg     912
Ser Ala Lys Val Val Ser Lys Ser Gly Val Leu Phe Phe Gly Leu Val
        290                 295                 300 ggc gat tca gct ctt ggc tgc tgg aac gaa cat cga aca ctt gaa aga     960
Gly Asp Ser Ala Leu Gly Cys Trp Asn Glu His Arg Thr Leu Glu Arg
```

```
                305                  310                  315
cac aat atc cgt acc gtc gct caa agt gat gag act ctt caa atg atc         1008
His Asn Ile Arg Thr Val Ala Gln Ser Asp Glu Thr Leu Gln Met Ile
320                 325                  330                 335 gct agc atg aag att aag gaa gct ctt cca cac gtg cct ata ttc gat         1056
Ala Ser Met Lys Ile Lys Glu Ala Leu Pro His Val Pro Ile Phe Asp
                340                  345                 350 agg tat ata aac cgt gaa tac ata ttg gtt tta agt aac aaa atg caa         1104
Arg Tyr Ile Asn Arg Glu Tyr Ile Leu Val Leu Ser Asn Lys Met Gln
            355                  360                 365 aaa atg gtg aat aat gac ttc aac ttc gac gat gtt aac ttc aga att         1152
Lys Met Val Asn Asn Asp Phe Asn Phe Asp Asp Val Asn Phe Arg Ile
        370                  375                 380 atg aac gcg aat gta aac gaa ttg ata ttg aac act cgt tgc gaa aat         1200
Met Asn Ala Asn Val Asn Glu Leu Ile Leu Asn Thr Arg Cys Glu Asn
    385                  390                 395 ccc gat aat gat cga aca cct ttc aaa att tca atc cat ttg taa             1245
Pro Asp Asn Asp Arg Thr Pro Phe Lys Ile Ser Ile His Leu
400                 405                 410

<210> SEQ ID NO 7
<211> LENGTH: 1830
<212> TYPE: DNA
<213> ORGANISM: Apis mellifera
<220> FEATURE:
<221> NAME/KEY: CDS
<222> LOCATION: (35)..(1666)
<220> FEATURE:
<221> NAME/KEY: sig_peptide
<222> LOCATION: (35)..(94)
<220> FEATURE:
<221> NAME/KEY: mat_peptide
<222> LOCATION: (95)..(1669)

<400> SEQUENCE: 7
gtcaattgga aaatatctgt attatcctag aaaa atg aca aag tgg ttg ttg ctg       55
                                     Met Thr Lys Trp Leu Leu Leu
                                     -20                 -15 gtg gtg tgc ctt ggt ata gct tgt caa gat gta aca agc gca gct gtg         103
Val Val Cys Leu Gly Ile Ala Cys Gln Asp Val Thr Ser Ala Ala Val
        -10                  -5                  -1 1 aat cat caa aga aaa tct gca aat aat ttg gca cat tct atg aaa gtg         151
Asn His Gln Arg Lys Ser Ala Asn Asn Leu Ala His Ser Met Lys Val
    5                   10                  15 atc tac gaa tgg aaa cac att gat ttt gat ttc ggt agc gat gaa aga         199
Ile Tyr Glu Trp Lys His Ile Asp Phe Asp Phe Gly Ser Asp Glu Arg
20                  25                  30                  35 aga gat gct gcg att aaa tct ggc gaa ttt gat cac aca aaa aat tat         247
Arg Asp Ala Ala Ile Lys Ser Gly Glu Phe Asp His Thr Lys Asn Tyr
                40                  45                  50 cct ttc gat gtg gac aga tgg cgt gat aag aca ttt gtc acc ata gaa         295
Pro Phe Asp Val Asp Arg Trp Arg Asp Lys Thr Phe Val Thr Ile Glu
            55                  60                  65 agg aac aat ggt gta cct tct tct ttg aac gtg gta act aat aaa aag         343
Arg Asn Asn Gly Val Pro Ser Ser Leu Asn Val Val Thr Asn Lys Lys
        70                  75                  80 ggc aaa ggt gga cct ctt cta cga cca tat cct gat tgg tcg ttt gcc         391
Gly Lys Gly Gly Pro Leu Leu Arg Pro Tyr Pro Asp Trp Ser Phe Ala
    85                  90                  95 aaa tac gaa gat tgc tct gga att gtg agc gct ttc aaa att gcg gtc         439
Lys Tyr Glu Asp Cys Ser Gly Ile Val Ser Ala Phe Lys Ile Ala Val
100                 105                 110                 115
```

| | | |
|---|---|---|
| gac aaa ttt gac aga tta tgg gtt ctg gac tca ggt ctt gtc aat aat<br>Asp Lys Phe Asp Arg Leu Trp Val Leu Asp Ser Gly Leu Val Asn Asn<br>120                         125                   130 | 487 |
| aat caa cct atg tgc tct cca aaa ttg tta acc ttt gat ctg aaa acc<br>Asn Gln Pro Met Cys Ser Pro Lys Leu Leu Thr Phe Asp Leu Lys Thr<br>            135                 140                    145 | 535 |
| tca aaa ttg gtt aag caa gtc gag ata cca cat aat att gcc gta aac<br>Ser Lys Leu Val Lys Gln Val Glu Ile Pro His Asn Ile Ala Val Asn<br>150                         155                   160 | 583 |
| gcc aca aca gga atg gga gaa tta gtt tca cta gct gtt caa gct ata<br>Ala Thr Thr Gly Met Gly Glu Leu Val Ser Leu Ala Val Gln Ala Ile<br>     165                 170                    175 | 631 |
| gat cgt acg aat act atg gtg tac ata gca gac gaa aaa ggc gaa ggt<br>Asp Arg Thr Asn Thr Met Val Tyr Ile Ala Asp Glu Lys Gly Glu Gly<br>180                       185               190            195 | 679 |
| tta atc atg tat caa aac tcc gac gat tcc ttc cat cga ttg act tcc<br>Leu Ile Met Tyr Gln Asn Ser Asp Asp Ser Phe His Arg Leu Thr Ser<br>               200                 205               210 | 727 |
| aat act ttc gat tac gat ccc aga tat acc aaa ttg aca gtc gct gga<br>Asn Thr Phe Asp Tyr Asp Pro Arg Tyr Thr Lys Leu Thr Val Ala Gly<br>            215                 220                225 | 775 |
| gaa agt ttc aca gtg aaa aat gga att tat gga att gca ctt agt ccc<br>Glu Ser Phe Thr Val Lys Asn Gly Ile Tyr Gly Ile Ala Leu Ser Pro<br>              230                 235               240 | 823 |
| gtg acg aac aat ctt tat tac agc cct ctt ctt tct cac ggt ttg tat<br>Val Thr Asn Asn Leu Tyr Tyr Ser Pro Leu Leu Ser His Gly Leu Tyr<br>     245                 250                   255 | 871 |
| tat gtt gat acg gaa caa ttc agc aat cca caa tat gaa gaa aat aac<br>Tyr Val Asp Thr Glu Gln Phe Ser Asn Pro Gln Tyr Glu Glu Asn Asn<br>260                       265               270            275 | 919 |
| gtg caa tat gaa gga tct caa gat att ttg aac act caa tca ttc ggt<br>Val Gln Tyr Glu Gly Ser Gln Asp Ile Leu Asn Thr Gln Ser Phe Gly<br>               280                 285               290 | 967 |
| aaa gta gta tcg aaa aat ggc gtc ctt ttc ttg gga ctc gtg ggt aat<br>Lys Val Val Ser Lys Asn Gly Val Leu Phe Leu Gly Leu Val Gly Asn<br>            295                 300                305 | 1015 |
| tca ggt att gcc tgc gtg aat gaa cat caa gta ctt cag aga gaa agt<br>Ser Gly Ile Ala Cys Val Asn Glu His Gln Val Leu Gln Arg Glu Ser<br>            310                 315               320 | 1063 |
| ttt gat gtt gtc gct cag aat gaa gag aca ctt caa atg atc gtt agt<br>Phe Asp Val Val Ala Gln Asn Glu Glu Thr Leu Gln Met Ile Val Ser<br>325                       330               335 | 1111 |
| atg aaa atc atg gaa aat ctt cca caa tcc ggc aga att aat gat cct<br>Met Lys Ile Met Glu Asn Leu Pro Gln Ser Gly Arg Ile Asn Asp Pro<br>340                       345               350            355 | 1159 |
| gaa ggc aat gaa tat atg ttg gct ttg agt aac aga atg caa aaa ata<br>Glu Gly Asn Glu Tyr Met Leu Ala Leu Ser Asn Arg Met Gln Lys Ile<br>               360                 365               370 | 1207 |
| ata aac aat gat ttt aat ttc aac gac gta aat ttc cga att ttg ggt<br>Ile Asn Asn Asp Phe Asn Phe Asn Asp Val Asn Phe Arg Ile Leu Gly<br>               375                 380               385 | 1255 |
| gcg aat gta gat gac tta atg aga aac act cgt tgc gga aga tat cac<br>Ala Asn Val Asp Asp Leu Met Arg Asn Thr Arg Cys Gly Arg Tyr His<br>            390                 395               400 | 1303 |
| aat cag aat gct ggc aat cag aat gct gac aat cag aat gct gac aat<br>Asn Gln Asn Ala Gly Asn Gln Asn Ala Asp Asn Gln Asn Ala Asp Asn<br>405                       410               415 | 1351 |
| cag aat gct aac aat cag aat gct gat aat cag aat gct aac aaa caa<br>Gln Asn Ala Asn Asn Gln Asn Ala Asp Asn Gln Asn Ala Asn Lys Gln<br>420                       425               430            435 | 1399 |

```
aat ggt aat aga caa aat gat aac aga cag aat gat aac aag caa aat      1447
Asn Gly Asn Arg Gln Asn Asp Asn Arg Gln Asn Asp Asn Lys Gln Asn
                440                 445                 450 ggt aac aga cag aat gat aac aag caa aat ggt aac aga cag aat gat      1495
Gly Asn Arg Gln Asn Asp Asn Lys Gln Asn Gly Asn Arg Gln Asn Asp
            455                 460                 465 aac aag caa aat ggt aac aga caa aat ggt aac aaa cag aat gat aac      1543
Asn Lys Gln Asn Gly Asn Arg Gln Asn Gly Asn Lys Gln Asn Asp Asn
        470                 475                 480 aag caa aat ggt aac aga cag aat gat aac aag agg aat ggt aac agg      1591
Lys Gln Asn Gly Asn Arg Gln Asn Asp Asn Lys Arg Asn Gly Asn Arg
    485                 490                 495 caa aat gat aat caa aat aat cag aat gat aat aat cga aat gat aat      1639
Gln Asn Asp Asn Gln Asn Asn Gln Asn Asp Asn Asn Arg Asn Asp Asn
500                 505                 510                 515 caa gtt cat cat tct tca aaa tta cat taaatcaatc aattatcaat            1686
Gln Val His His Ser Ser Lys Leu His
                520 taaaatcaat taattaagat gtaaatcaaa ttatttttta aaatattttt tcgatgtaaa    1746 caaaattttg taaatctttt cattatatta taaataaata aaataaatat cgttttcgca    1806 taaaaaaaaa aaaaaaaaaa aaaa                                           1830

<210> SEQ ID NO 8
<211> LENGTH: 1430
<212> TYPE: DNA
<213> ORGANISM: Apis mellifera
<220> FEATURE:
<221> NAME/KEY: CDS
<222> LOCATION: (46)..(1341)
<220> FEATURE:
<221> NAME/KEY: sig_peptide
<222> LOCATION: (46)..(102)
<220> FEATURE:
<221> NAME/KEY: mat_peptide
<222> LOCATION: (103)..(1341)
<220> FEATURE:
<221> NAME/KEY: Unsure
<222> LOCATION: (1134)..(1134)
<223> OTHER INFORMATION: n is a, c, g, or t

<400> SEQUENCE: 8
ttcacgtaca atattccatt gcttcgttac tcgcagctta gaaaa atg aca aga ttg     57
                                                 Met Thr Arg Leu ttt atg ctg gta tgc ctt ggc ata gtt tgt caa ggt acg aca ggc aac     105
Phe Met Leu Val Cys Leu Gly Ile Val Cys Gln Gly Thr Thr Gly Asn
-15                 -10                 -5                 -1   1 att ctt cga gga gag tct tta aac aaa tca tta ccc atc ctt cac gaa     153
Ile Leu Arg Gly Glu Ser Leu Asn Lys Ser Leu Pro Ile Leu His Glu
            5                   10                  15 tgg aaa ttc ttt gat tat gat ttc ggt agc gat gaa aga aga caa gat     201
Trp Lys Phe Phe Asp Tyr Asp Phe Gly Ser Asp Glu Arg Arg Gln Asp
        20                  25                  30 gca att cta tct ggc gaa tac gac tac aag aat aat tat cca tcc gac     249
Ala Ile Leu Ser Gly Glu Tyr Asp Tyr Lys Asn Asn Tyr Pro Ser Asp
    35                  40                  45 att gac caa tgg cat gat aag att ttt gtc acc atg ctg aga tac aat     297
Ile Asp Gln Trp His Asp Lys Ile Phe Val Thr Met Leu Arg Tyr Asn
50                  55                  60                  65 ggc gta cct tcc tct ttg aac gtg ata tct aaa aag gtc ggt gat ggt     345
Gly Val Pro Ser Ser Leu Asn Val Ile Ser Lys Lys Val Gly Asp Gly
                70                  75                  80
```

```
ggt cct ctt cta caa cct tat ccc gat tgg tcg ttt gct aaa tat gac      393
Gly Pro Leu Leu Gln Pro Tyr Pro Asp Trp Ser Phe Ala Lys Tyr Asp
        85              90              95 gat tgc tct gga atc gtg agc gcc tca aaa ctt gcg atc gac aaa tgc      441
Asp Cys Ser Gly Ile Val Ser Ala Ser Lys Leu Ala Ile Asp Lys Cys
100             105             110 gac aga ttg tgg gtt ctg gac tca ggt ctt gtc aat aat act caa ccc      489
Asp Arg Leu Trp Val Leu Asp Ser Gly Leu Val Asn Asn Thr Gln Pro
115             120             125 atg tgt tct cca aaa ctg ctc acc ttt gat ctg act acc tcg caa ttg      537
Met Cys Ser Pro Lys Leu Leu Thr Phe Asp Leu Thr Thr Ser Gln Leu
130             135             140             145 ctc aag caa gtt gaa ata cca cat gat gtt gcc gta aat gcc act aca      585
Leu Lys Gln Val Glu Ile Pro His Asp Val Ala Val Asn Ala Thr Thr
                150             155             160 gga aag gga aga tta tca tct cta gct gtt caa tct tta gat tgc aat      633
Gly Lys Gly Arg Leu Ser Ser Leu Ala Val Gln Ser Leu Asp Cys Asn
            165             170             175 aca aat agc gat act atg gtg tac ata gca gac gag aaa ggt gaa ggt      681
Thr Asn Ser Asp Thr Met Val Tyr Ile Ala Asp Glu Lys Gly Glu Gly
        180             185             190 tta atc gtg tat cat aat tct gat gat tcc ttc cat cga ttg act tcc      729
Leu Ile Val Tyr His Asn Ser Asp Asp Ser Phe His Arg Leu Thr Ser
        195             200             205 aac act ttc gat tac gat cct aaa ttt acc aaa atg acg atc gat gga      777
Asn Thr Phe Asp Tyr Asp Pro Lys Phe Thr Lys Met Thr Ile Asp Gly
210             215             220             225 gaa agt tac aca gcc caa gat gga att tct gga atg gct ctt agt ccc      825
Glu Ser Tyr Thr Ala Gln Asp Gly Ile Ser Gly Met Ala Leu Ser Pro
                230             235             240 atg act aac aat ctc tat tac agt cct gta gct tcc acc agt ttg tat      873
Met Thr Asn Asn Leu Tyr Tyr Ser Pro Val Ala Ser Thr Ser Leu Tyr
            245             250             255 tat gtt aac acg gaa caa ttc aga aca tcc gat tat caa cag aat gac      921
Tyr Val Asn Thr Glu Gln Phe Arg Thr Ser Asp Tyr Gln Gln Asn Asp
        260             265             270 ata cat tac gaa gga gtc caa aat att ttg gat acc caa tcg tcc gct      969
Ile His Tyr Glu Gly Val Gln Asn Ile Leu Asp Thr Gln Ser Ser Ala
    275             280             285 aaa gta gta tca aag agt ggc gtt ctc ttc ttc gga ttg gtg ggc gat     1017
Lys Val Val Ser Lys Ser Gly Val Leu Phe Phe Gly Leu Val Gly Asp
290             295             300             305 tca gct ctt ggc tgc tgg aac gaa cat cga aca ctt gaa aga cac aat     1065
Ser Ala Leu Gly Cys Trp Asn Glu His Arg Thr Leu Glu Arg His Asn
                310             315             320 atc cgt acc gtc gct caa agt gat gag act ctt caa atg atc gct agc     1113
Ile Arg Thr Val Ala Gln Ser Asp Glu Thr Leu Gln Met Ile Ala Ser
            325             330             335 atg aag att aag gaa gct ctn cca cac gtg cct ata ttc gat agg tat     1161
Met Lys Ile Lys Glu Ala Xaa Pro His Val Pro Ile Phe Asp Arg Tyr
        340             345             350 ata aac cgt gaa tac ata ttg gtt tta agt aac aaa atg caa aaa atg     1209
Ile Asn Arg Glu Tyr Ile Leu Val Leu Ser Asn Lys Met Gln Lys Met
    355             360             365 gtg aat aat gac ttc aac ttc gac gat gtt aac ttc aga att atg aac     1257
Val Asn Asn Asp Phe Asn Phe Asp Asp Val Asn Phe Arg Ile Met Asn
370             375             380             385 gcg aat gta aac gaa ttg ata ttg aac act cgt tgc gaa aat ccc gat     1305
Ala Asn Val Asn Glu Leu Ile Leu Asn Thr Arg Cys Glu Asn Pro Asp
                390             395             400
```

```
aat gat cga aca cct ttc aaa att tca atc cat ttg taaaatctga          1351
Asn Asp Arg Thr Pro Phe Lys Ile Ser Ile His Leu
        405                     410 gtttttgtt atatattaaa tatttctcga aatttcttc cattatgaat gtataaaata     1411
aatattgttt tcgcataat                                                 1430

<210> SEQ ID NO 9
<211> LENGTH: 24
<212> TYPE: DNA
<213> ORGANISM: Artificial
<220> FEATURE:
<223> OTHER INFORMATION: Oligonucleotide as PCR sense primer

<400> SEQUENCE: 9
cctagaaaaa tgacaaagtg gttg                                          24

<210> SEQ ID NO 10
<211> LENGTH: 26
<212> TYPE: DNA
<213> ORGANISM: Artificial
<220> FEATURE:
<223> OTHER INFORMATION: Oligonucleotide as PCR anti-sense primer

<400> SEQUENCE: 10
gattttacaa aattttgttt acatcg                                        26

<210> SEQ ID NO 11
<211> LENGTH: 28
<212> TYPE: DNA
<213> ORGANISM: Artificial
<220> FEATURE:
<223> OTHER INFORMATION: Oligonucleotide as PCR sense primer

<400> SEQUENCE: 11
gctacatatg aacattcttc gaggagag                                      28

<210> SEQ ID NO 12
<211> LENGTH: 35
<212> TYPE: DNA
<213> ORGANISM: Artificial
<220> FEATURE:
<223> OTHER INFORMATION: Oligonucleotide as PCR anti-sense primer

<400> SEQUENCE: 12
gctaggatcc ctattacaaa tggattgaaa ttttg                              35
```

ANTIALLERGIC AGENT

This application is a 371 of PCT/JP03/10795 filed on Aug. 26, 2003.

TECHNICAL FIELD

The present invention relates to an anti-allergic agent, more particularly, to an anti-allergic agent comprising, as effective ingredients, proteins obtainable from intact royal jelly or purified royal jelly, and to an anti-allergic agent comprising intact royal jelly or purified royal jelly which contains the proteins.

BACKGROUND ART

In these days, change in diet, etc. has brought a problem of increasing patients suffering from allergic diseases. Particularly, the increase of atopic diseases such as pollinosis, atopic dermatitis, bronchial asthma, allergic rhinitis and contact hypersensitivity has become to be a serious problem. Anti-histamic agents or steroids have been usually administered to symptomatically treat allergic diseases. However, such agents have a problem of causing serious side effects in their long-term use. Under these circumstances, a method for treating allergic diseases, which enables to effectively alleviate various symptoms thereof and which is applicable for a long-term use without affecting daily life, has been desired.

Recently, royal jelly (may be abbreviated as "RJ", hereinafter) has been arousing public interest as a health food, while its various biological activities have been confirmed. Royal jelly is known to be a milky secretion from the exocrine of worker bees, and it is stored in queen cells in beehives, and it is a food for a larva to become a queen bee. Varying depending on its origin and harvesting season, the composition of royal jelly is known to be slightly changed in the range of 65–75% of water, 15–20% of proteins, 10–15% of carbohydrates, 1.7–6% of fats, and 0.7–2% of ash. J. Schimitzova et al. has succeeded to clone cDNAs of five major proteins contained in royal jelly using honeybee (*Apis mellifera*) and revealed their nucleotide sequences and putative amino acid sequences. The five proteins were named as "MRJP1", "MRJP2", "MRJP3", "MRJP4", and "MRJP5" by abbreviating the following capitals of "major royal jelly protein". However, these proteins have not yet been studied on their biological activities.

Under the above circumstances, the present invention has an object to provide a method for effectively alleviating various symptoms caused by allergic diseases without causing serious side effects when applied to patients in need thereof.

DISCLOSURE OF THE INVENTION

The present inventors have eagerly studied on royal jelly to attain the above object. As a result, they revealed that a kind of low-molecular or high-molecular component, concretely, a protein having a partial amino acid sequence of SEQ ID NO: 1 or 2, remarkably inhibits the production of antibodies and/or cytokines in living bodies, and confirmed that it effectively alleviates various symptoms caused by allergic diseases without serious side effects.

The present invention solves the above object by providing an anti-allergic agent comprising the proteins obtained from intact royal jelly or a purified royal jelly, and anti-allergic agent comprising intact royal jelly or purified royal jelly which contains the proteins.

Also, the present invention solves the above object by providing foods and beverages comprising the above anti-allergic agent.

Further, the present invention solves the above problem by providing cosmetics comprising the above anti-allergic agent.

Furthermore, the present invention solves the above problem by providing pharmaceuticals comprising the above anti-allergic agent.

(Closed circles mean data of five each mouse, "–" means average, "*" means data having significantly different data by 5% or less of relative risk.)

Figure 5:
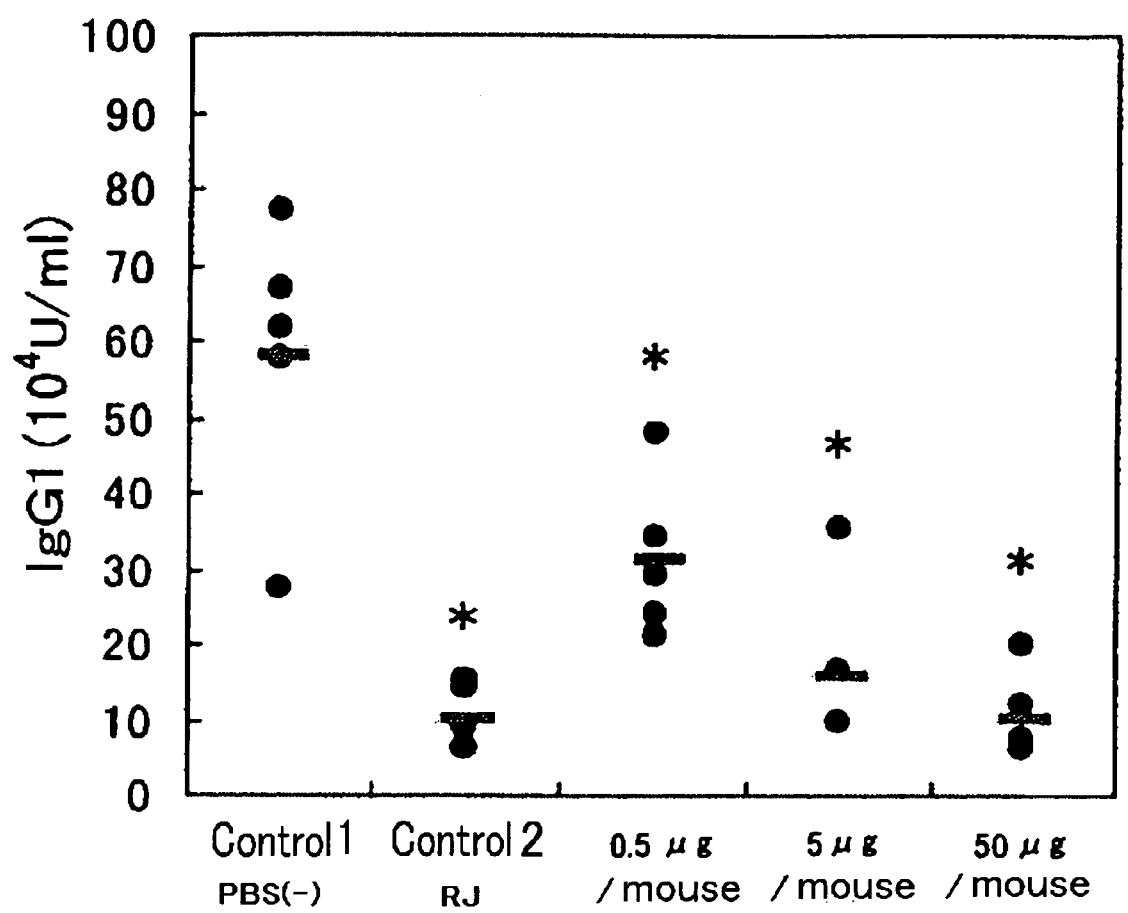

FIG. 5 shows a result of measuring anti-OVA IgG1 antibody value in serum of OVA/Alum immunized male BALB/c mouse when intraperitoneally administered with royal jelly or "RJP70".

(Closed circles mean data of five each mouse, "–" means average, "*" means data having significantly different data by 5% or less of relative risk.)

BEST MODE FOR CARRYING OUT THE INVENTION

The present invention relates to an anti-allergic agent comprising, as effective ingredients, proteins obtainable from intact royal jelly or purified royal jelly or to an anti-allergic agent comprising intact royal jelly or purified royal jelly containing the proteins. Royal jelly usable in the present invention is of that secreted from honeybees such as *Apis mellifera, Apis cerana, Apis dorsata* and *Apis florea*, and it is produced in Japan, South America, North America, Australia, China or Europe. Any royal jelly different in form, purity or preparation can be arbitrarily used as long as it comprises a low-molecular or high-molecular component having an anti-allergic effect. Particularly, such a component is a protein having a partial amino acid sequence of SEQ ID NO: 1 or 2 has an effect on treatment or prevention of allergic diseases such as atopic allergy, tissue specific allergy, immune complex allergy and delayed type allergy when applied to mammals including humans selectively after through appropriate purification.

Royal jelly can be purified by applying usual purification methods for other low-molecular or high-molecular biologically active substances when it has not enough anti-allergic activity. The term "purified royal jelly" as referred to as in the present invention means those having a higher content of an objective ingredient on a dry solid basis purified by partially removing some of unnecessary ingredients from a raw royal jelly. As such a water-soluble protein fraction of a royal jelly is preferably used in the present invention. Examples of such purification method is illustrated with filtration, concentration, dry, centrifugation, sedimentation, salting out, dialysis, ion-exchange chromatography, gel filtration chromatography, adsorption chromatography, isoelectric chromatography, hydrophobic chromatography, reverse-phase chromatography, affinity chromatography, gel electrophoresis and isoelectric electrophoresis, and optionally, applied with an appropriate combination thereof.

The anti-allergic components contained in royal jelly used in the present invention can be illustrated with proteins having a partial amino acid sequence of SEQ ID NO: 1 or 2. Any protein can be used in the present invention as long as it has partial amino acid sequence represented by SEQ ID NO: 1 or 2 and give an anti-allergic effect on living bodies regardless of its purity, origin and preparation. A preferable protein having biological effect on inhibiting the production of antibodies and/or cytokines is one comprising a partial amino acid sequence represented by SEQ ID NO: 1 or 2 and having a molecular weight of 55,000–70,000 Daltons on SDS-polyacrylamide gel electrophoresis (SDS-PAGE). More preferable one is a protein comprising an amino acid sequence of SEQ ID NO: 3 or 4. Such proteins comprising the above amino acid sequences are extremely useful in the present invention because they remarkably inhibit the production of antibodies and cytokines in living bodies and alleviate various symptoms caused by allergic diseases effectively without causing serious side effects in a relatively long-term administration. The proteins used in the present invention are not restricted to the above-identified proteins. For example, one or more amino acid residues of proteins having the whole amino acid sequence of SEQ ID NO: 3 or 4 can be deleted or replaced with other amino acid residues or one or more amino acids can be inserted in or added to the amino acid sequence of SEQ ID NO: 3 or 4 in such a manner of not substantially eliminating the anti-allergic effect.

The anti-allergic protein having a partial amino acid sequence of SEQ ID NO: 1 or 2 used in the present invention is originated from royal jelly and can be usually obtained from natural royal jelly. The anti-allergic protein can be used after purifying royal jelly as a raw material in a desired level by one or more purification methods. The term "isolated or partially-purified protein having a partial amino acid sequence of SEQ ID NO: 1 or 2" means a protein purified and isolated perfectly or purified partially using purification methods. Such proteins can be advantageously used in the present invention.

Figure 1:
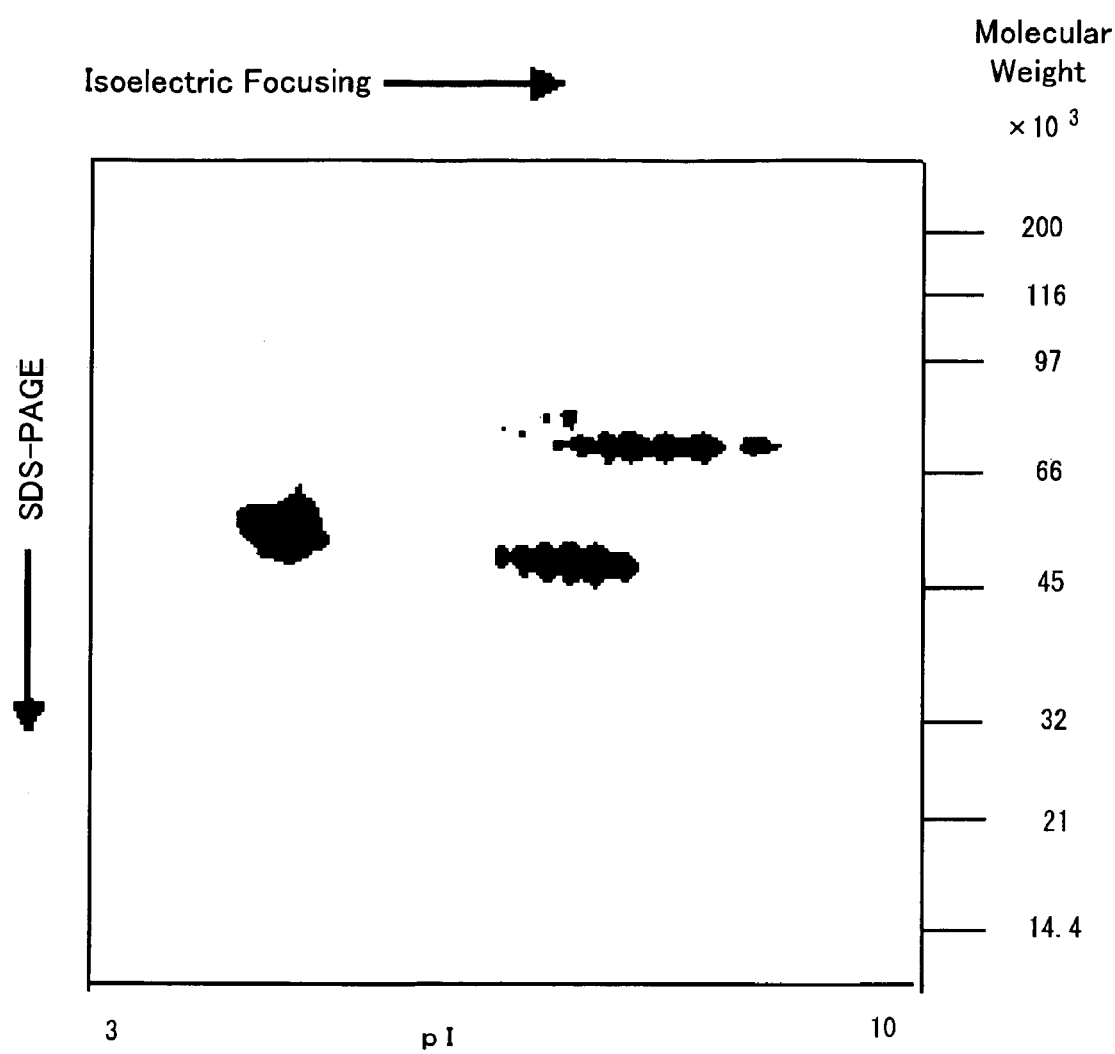
FIG. 1 shows a two-dimensional electrophoresis pattern of anti-allergic proteins of the present invention contained in a raw royal jelly.

The protein having a partial amino acid sequence of SEQ ID NO: 1 or 2 is identified or quantified by measuring its molecular weight using electrophoresis. Examples of electrophoresis are usually illustrated with SDS-PAGE in the presence of a reducing agent, electrofocusing, and two-dimensional electrophoresis in combination thereof. FIG. 1 shows the result of detection for an anti-allergic protein by two-dimensional electrophoresis. The proteins having a partial amino acid sequence of SEQ ID NO: 1 contained in royal jelly have a molecular weight of about 70 kilo-Daltons (kDa) as a major protein and a molecular weight of about 55 kDa as a minor protein on SDS-PAGE in the presence of a reducing agent. The proteins having a partial amino acid sequence of SEQ ID NO: 2 contained in royal jelly have a molecular weight of about 55 kDa on SDS-PAGE in the presence of reducing agent. Hereinafter, in the present specification, the proteins having the amino acid sequence of SEQ ID NO: 3 of proteins having a partial amino acid sequence of SEQ ID NO: 1 corresponds to the protein called "Active Protein No. 1-2" or "RJP70", and the protein having the amino acid sequence of SEQ ID NO: 4 of the proteins having a partial amino acid sequence of SEQ ID NO: 2 corresponds to the protein called "Active Protein No. 2" or "RJP55".

As described above, "RJP70" and "RJP55" used as anti-allergic proteins in the present invention have the amino acid sequence of SEQ ID NOs: 3 and 4, respectively. Comparing the amino acid sequences of these proteins with major royal jelly proteins "MRJP1", "MRJP2", "MRJP3", "MRJP4" and "MRJP5" disclosed by J. Schimitzova et al., in "*Cellular and Molecular Life Sciences*", Vol. 54, pp. 1,020–1,030, (1998); "RJP70" and "RJP55" were completely identical with "MRJP3" and "MRJP1" at least in their N-terminal regions. Further, J. Schimitzova et al. have reported some variants of "MRJP3" showing a molecular weight of 60, 63, 66 or 70 kDa. The protein having a partial amino acid sequence of SEQ ID NO. 1 used in the present invention showed both molecular weights of about 70 kDa ("RJP70") and about 55 kDa. While, "RJP55" has the same N-terminal amino acid sequence and molecular weight (55 kDa) as of "MRJP1". They reported that "MRJP1" and "MRJP3" dominated about 31% and 26% of the total amount of royal jelly proteins, respectively. Therefore, "RJP70" and "RJP55" are possibly substantially the same proteins as "MRJP3" and "MRJP1", respectively. However, these proteins have not been studied about their biological activity such as anti-allergic activity at all.

Recombinant DNA technology using a DNA encoding the amino acid sequence of SEQ ID NO: 3 or 4 is applicable for preparing the anti-allergic protein as well as a method of extracting from natural royal jelly. Honeybees are used as an advantageous material for a source of DNA such as mRNA and genomic DNA. The DNA encoding anti-allergic protein "RJP70" or "RJP55" is illustrated with the cloned DNA having the nucleotide sequence of SEQ ID NO: 5 or 6. While, the nucleotide sequences and amino acid sequences of "MRJP3" and "MRJP1", which have been a quite high similarity to "RJP70" and "RJP55", respectively, can be referred to "GenBank" gene database as Accession Nos. Z26318 (SEQ ID NO: 7) and AF000633 (SEQ ID NO:8).

The following evidences were revealed by comparing the nucleotide sequences of the DNA encoding "RJP70" or "RJP55" cloned from *Apis mellifera* with that of "MRJP3" (SEQ ID NO: 7) or "MRJP1" (SEQ ID NO:8). There are five different nucleotides and three different putative amino acid residues due to different nucleotides between "RJP70" and "MRJP3". While, the nucleotide sequence of the DNA encoding "RJP55" completely corresponds to that of "MRJP1", although the 1134th base of the nucleotide sequence of "MRJP1" was described unknown, but it would correspond to thymidine "t" in "RJP55". These differences are summarized in Table 1.

TABLE 1

|  | Number of Position | Protein RJP70 | MRJP3 |
|---|---|---|---|
| Position of Different Nucleotides* | 770 | G | A |
|  | 819 | C | T |
|  | 820 | T | C |
|  | 821 | C | T |
|  | 861 | G | C |
| Positions of Different Amino Acid Residues** | 237 | Cys | Tyr |
|  | 254 | Ser | Leu |
|  | 267 | Arg | Ser |

*The numbering starts from "A" of the starting codon "ATG".
**The numbering is based on the amino acid sequence of "RJP70" and it starts from "Ala" at the N-terminus.

The anti-allergic protein used in the present invention usually consists of the amino acid sequence completely encoded by the nucleotide sequence of SEQ ID NO: 5 or 6. It also can comprise any amino acid sequence partially encoded by the nucleotide sequence of SEQ ID NO: 5 or 6 as long as it comprises the amino acid sequence of either SEQ ID NO: 1 or 2. The amino acid sequence of the protein can be advantageously altered by deletion, replacement, insertion and/or addition of one or more amino acid residues according to usual recombinant DNA technique such as site specific mutagenesis in such a manner that the anti-allergic activity of the protein originally encoded by the DNA is not substantially eliminated. To keep anti-allergic activity, the altering percentage of the amino acid sequence of the protein is preferably limited to less than about 35% of the whole the amino acid sequence in view of about 66% amino acid homology between "RJP70" and "RJP55".

The DNA having a nucleotide sequence of SEQ ID NO: 5 or 6 is useful for producing the protein as an effective ingredient of the anti-allergic agent of the present invention according to recombinant DNA technique: The anti-allergic protein can be obtained by artificially expressing the DNA having the nucleotide sequence of SEQ ID NO: 5 or 6 encoding "RJP70" or "RJP55" and then collecting the resulting protein. To express the above DNA, a method of breeding or culturing an appropriate host cell transformed with the DNA or in vitro DNA expression system (in vitro translation and in vitro transcription) can be selectively used.

The transformant for producing "RJP70" or "RJP55" used in the present invention is usually obtained by transforming an appropriate host with the recombinant DNA inserted with the DNA having the nucleotide sequence of SEQ ID NO: 5 or 6 in an autonomously replicable vector DNA. The autonomously replicable vector can be selected from usual vectors suitable to the employed host. Such usual vectors are plasmid vectors illustrated with pBR322, pUC18, Bluescript II SK (+), pUB110, pTZ4, pC194, pHV14, TRp7, YEp7 and pBS7; phage vectors illustrated with λgt·λC, λgt·λB, ρ11, φ1 and φ105; and baculovirus vectors illustrated with pVL1393. When expressing the DNAs of the present invention, pUC118, pUC119, pUC18, pUC19, pBR322, Bluescript II SK(+), λgt·λC and λgt·λB are suitable for *E. coli*, and, pUB110, pTZ4, pC194, ρ11, φ1 and φ105 are suitable for *Bacillus subtilis*. In the case of replicating the recombinant DNA in two or more hosts, pHV14, TRp7, YEp7 and pBS7 are useful. Such autonomously replicable vectors usually have appropriate nucleotide sequences such as a promoter, enhancer, replication origin, transcription termination site and selection marker sequence for expression of the DNAs of the present invention in each host or for confirmation of a desired transformant. To insert the DNAs in such vectors, any usual technique in the art can be used; such technique can be illustrated with addition of a linker, addition of a restriction enzyme recognition site by PCR method, and treatment with a restriction enzyme or ligase.

Any host cells in the art can be used for transforming with the DNAs of the present invention; such host cells can be illustrated with microorganisms such as *E. coli, Bacillus subtilis*, yeasts and fungus; non-vertebrate cells such as insect; plant cell, and vertebrate cell. Since insect cells are enable to provide a more natural protein, they are more preferably used. Such host cells can be introduced with the DNAs of the present invention by applying suitable methods such as phosphate calcium method, electroporation method, virus infection method, DEAE-dextran method, lipofection method, and microinjection method. A desired transformant is cloned from the resulting transformants by checking the presence of the DNAs or the production of an anti-allergic protein. The materials and techniques for obtaining the recombinant DNAs and transformants described above have been taught by J. Sambruk et al. in "*MOLECULAR CLONING A LABORATORY MANUAL*", 2nd edition, published by Cold Spring Harbor Laboratory, (1989).

The transformants thus obtained produce anti-allergic proteins intracellulary or extracellulary when cultured under an appropriate condition suitable for the vectors used. Usual culture media containing carbon sources, nitrogen sources and minerals, optionally supplemented with amino acids or vitamins as a micronutrient can be used. The carbon sources are illustrated with sugar sources such as starch, starch hydrolysate, glucose, fructose, sucrose and trehalose. The nitrogen sources are illustrated with nitrogenous non-organic or organic compound such as ammonia or salts thereof, urea, nitrates, peptones, yeast extracts, defatted soybeans, corn steep liquors and meat extracts. Varying with the host cell or the kind of vectors, a used culture containing anti-allergic protein is obtained by culturing a host cell for about one to six days under the condition kept at 20–60° C. and pH 2–10.

The protein obtained by the above recombinant DNA techniques can be used without purification. However, it is usually purified in an appreciate manner to be suitable for its use. Such purification methods for the protein can be chosen from usual methods described in the case of preparation for natural royal jelly.

Proteins, having as a partial amino acid sequence of either SEQ ID NO: 1 or 2 used in the present invention, exhibit a biological activity for inhibiting the production of antibodies or cytokines. The present inventors achieved to identify of proteins, which are main substances for anti-allergic activity of royal jelly, as "RJP70" and "RJP55" by separately purifying the proteins from royal jelly as tracing the activity of inhibiting the production of cytokines in spleen cells from mouse immunized with Alum adjuvant and stimulated with anti CD3 antibody. Similarly as in the case of natural royal jelly, they can be advantageously used to inhibit the onset of allergy induced by an increased production of the above cytokines and antibodies, and relative and treat the symptoms thereof after the onset, since these proteins have been determined in vitro and in vivo tests to inhibit the production of various cytokines and antibodies such as IL-2, IL-4, IFN-γ, TNF-α, IgE and IgG.

The more the anti-allergic agent of the present invention contains a protein comprising the partial amino acid sequence of SEQ ID NO: 1 or 2 as an anti-allergic ingredient, the more it remarkably exhibits the anti-allergic effect.

The agent can contain an anti-allergic substance, which has been highly or partially purified or in an intact natural form. The agent preferably contains the protein as an anti-allergic ingredient in a sufficient amount to decrease the relative production of IL-2 to 80% or less or of IL-4 to 60% or less compared to the case lack of the protein when determined by the inhibition test of cytokine production with 2 mg/ml protein concentration described in the following Experiment.

The anti-allergic agent of the present invention effectively alleviates various symptoms caused by allergic diseases, particularly, atopic diseases. The atopic diseases are kind of hypersensitive diseases appearing congenitally and family in various organs, which is illustrated with dermatitis, hay fever, bronchial asthma, urticaria, allergic rhinitis, insect allergy and mite allergy, as well as a disease caused by type I allergic reaction with immunogloblin E (IgE).

The following explains uses of the anti-allergic agent of the present invention. The agent can perform the desired anti-allergic effect in an oral or parental administration. An effective dose of the agent can be decided according to kind, age or sex of the objective mammals including humans. When the protein having a partial amino acid sequence of SEQ ID NO: 1 or 2 is used as an effective ingredient, it is orally taken or administrated in an amount of usually 0.01–100 mg/dose, preferably 0.1–50 mg/dose. While observing its effect, the intake or administration is carried out once a day or several times a day on successive days or one or more interval days. The intake or administration is not specifically restricted. For example, it can be optionally chosen from oral route, tube feeding route, percutaneous route, transmucosal route, intravenous route, etc. When the agent is used as an oral anti-atopic agent formed in a food or beverage, more appropriate royal jelly material can be provided in view of economical use by measuring the activity for inhibiting the production of cytokines in some natural royal jelly materials according to the following Experiment 2.

When the anti-allergic agent of the present invention can be prepared as an external agent which is directly applied to the skin such as cosmetics, it contains the anti-allergic ingredient from royal jelly having the amino acid sequence of SEQ ID NO: 1 or 2 in an amount of 0.001 to 10% by weight, preferably, 0.01 to 1% by weight to the total weight of the external agent. It can be directly applied to the skin once a days or one more interval days while observing the effect. The amount of less than 0.001% by weight may be hard to exhibit the effect. The amount of over 10% by weight may not be preferable in view of economical use because of its lesser effect than expected. Usually, the agent contains the ingredient in the above range.

The allergic agent of the present invention can be advantageously used in the form of a composition illustrated with foods, beverages, cosmetics or pharmaceuticals. Optionally, the composition can be incorporated with other ingredients having an anti-allergic effect illustrated with a product of labiate or Pfaffia together with royal jelly or anti-allergic proteins. The resulting composition is usually usable in the field of foods, beverages, cosmetics or pharmaceuticals. Further, optionally, the composition may further contain one or more other ingredients than the ingredients described above, for example, water, alcohols, starch, proteins, amino acids, dietary fibers, carbohydrates, lipids, vitamins, minerals, flavors, colorants, sweeteners, seasonings, spices, antiseptics, emulsifiers, surfactants, excipients, fillers, gums, or preservatives. Varying depending on the necessity for the composition in the field, the suitable ingredients can be selected from the above ingredients. The composition containing such ingredients is not restricted to a specific form. It can be provided in the desirable form such as a powder, granule, tablet, paste, jelly, milky lotion or solution.

The above carbohydrates are illustrated with saccharides such as glucose, fructose, lactose, trehalose, maltose, sucrose, lactosucrose, and starch syrup; cyclic saccharides such as cyclodextrins and cyclic tetrasaccharide; sugar alcohols such as erythritol, mannitol, sorbitol, xylitol, maltitol, and hydrogenated starch syrup; high intensity sweeteners such as aspartame, stevia extract and sucralose; natural polysaccharides such as pullulan and carrangeenan; gums such as natural gums and synthesized carboxymethylcellulose. One or more of such ingredients can be advantageously used for forming into a product in a solid form and for stabilizing the agent improving its taste, and retaining its flavor.

The compositions containing the anti-allergic agent of the present invention can be produced in considering with objective animals and intake or administration methods. It can be produced by admixing the anti-allergic agent of the present invention with one or more ingredients acceptable in the field of foods, beverages, cosmetics, pharmaceuticals, quasi-drugs, feeds, baits or pet foods in a proper proportion, and optionally, diluting, concentrating, drying, filtrating or centrifuging, and then forming desirably. The order of adding each ingredient and the timing of such processes are not specifically restricted as long as they do not lose the anti-allergic activity of the agent.

In the case of using the composition containing the anti-allergic agent of the present invention as a food, it is illustrated with frozen desserts such as ice creams, ice candies and sherbets; syrups such as sugar syrups; spreads or pastes such as butter creams, custard creams, flour pastes, peanut pastes and fruit pastes; western confectionaries such as chocolates, jellies, candies, gummy jellies, caramels, chewing gums, custard puddings, cream puffs, and sponge cakes; processing fruits or vegetables such as jams, marmalades, syrups, and pickles; Japanese confectionaries such as "manju" (Japanese-style bun stuffed with "azuki"-bean paste), "uiro" (sweetened Japanese-style rice jelly), "an" ("azuki"-bean paste, sweet bean jelly), soft "azuki"-bean jellies, sponge cakes, and hard candies; seasonings such as soy sauces, powdered soy sauces, "miso" (Japanese-style bean paste), powdered "miso", mayonnaises, dressings, vinegars, "san-bai-zu" (a sauce of sugar, soy sauce and vinegar), table sugars, and coffee sugars. In the case of using it as a beverage, it is illustrated with alcoholic drinks such as synthetic "sake", brews, fruit wines, and Western liquors; soft drinks such as juices, mineral waters, soda waters, lactic acid drinks, lactic acid bacteria beverages, sport drinks, nutritious supplement drinks, green teas, black teas, oolong teas, coffees, and cocoas.

In the case of using the agent as a cosmetic, it is prepared in the form of a lotion, cream, milky lotion, gel, powder, paste, or block. It is illustrated with cosmetics for cleaning such as soaps, cosmetic soaps, cleansing powders, face wash creams, face wash foams, facial rinses, body shampoos, body rinses, hair shampoos, hair rinses, and hair cleansing powders; cosmetics for hair such as set lotions, hair blows, stick pomades, hair creams, pomades, hair sprays, hair liquids, hair tonics, hair lotions, hair restorers, hair dyes, treatments for scrap, hair cosmetics, gloss-imparting hair oils, hair oils and combing oils; base cosmetics such as cosmetic lotions, vanishing creams, emollient creams, emollient lotions, cosmetic packs in the form of a jelly peel off, jelly wiping, paste washing or powders, cleansing creams, cold creams, hand creams, hand lotions, milky lotions, moisture-imparting liquids, after-shaving lotions, shaving lotions, before-shaving lotions, after-shaving foams, after-shaving creams, before-shaving creams, cosmetic oils, and baby oils; makeup cosmetics such as foundations in the form of a liquid, cream or solid, talcum powders, baby powders, body powders, perfume powders, makeup bases, face powders in the form of a cream, paste, liquid, solid or powder, eye shadows, eye creams, mascaras, eyebrow pencils, eyelash makeup, rouges, and rouge lotions; perfume cosmetics such as perfumes, paste perfumes, powder perfumes, eau de colognes, perfume colognes, and eau de toilette; suntan and suntan preventive cosmetics such as suntan creams, suntan lotions, suntan oils, suntan preventive creams, suntan preventive lotions, and suntan preventive oils; nail cosmetics such as manicures, pedicures, nail colors, nail laqcuers, enamel removers, nail creams, and nail dressings; eyeliner cosmetics; rouges and lipsticks such as lipsticks, lip creams, paste rouges, and lip-glosses; oral cosmetics such as tooth pastes and mouse washes; bath cosmetics such as bath salts, bath oils and bath cosmetic materials.

In the case of using the agent as a pharmaceutical, it is illustrated with extracts, elixirs, capsules, granules, pills, ointments for eye, oral mucosal patches, suspensions, emulsions, plasters, suppositories, powders, ethanol preparations, tablets, syrups, injections, tinctures, eye drops, ear drops, nasal drops, trochees, ointments, aromatic water, nasal nebulas, lemonades, liniments, fluid extracts, lotions, poultices, air sprays, embrocations, bath preparations, adhesive preparations, pastes, and cataplasms. The composition used in the above form can be produced according to usual processing manner suitable for desired product by adding the anti-allergic agent to the composition at an appropriate timing. If the desired product is a composition produced through some heating processes, the agent should not be added to the composition before the last heating process to avoid the decrease of the anti-allergic activity. Concretely, the agent should be added to the composition after cooled down to 30° C., preferably, normal temperature after the last heating process. Such composition usually contains the anti-allergic agent in the amount of 0.01% by weight or more, preferably, 0.1 to 100% by weight.

The anti-allergic agent of the present invention used as a pharmaceutical for treating or preventing allergic diseases can be applied to metal allergy, delayed contact hypersensitivity, food allergy, drug allergy, and chemical sensitivity, as well as general atopic diseases as described above. Since the agent inhibits the production of IL-2, IL-4, IFN-γ and TNF-α, it is useful for alleviating or treating the autoimmune diseases such as multiple sclerosis, polymyositis, rheumatoid arthritis, rheumatoid arthritis, scleroderma, polyarteritis nodosa, active chronic hepatitis, atrophic gastritis, autoimmune hemolytic anemia, azoospermia, Basedow disease, Behçet disease, CRTS syndrome, cold agglutinin hemolytic anemia, ulcerative colitis, Goodpasture syndrome, hyperthyroidism, chronic thyroiditis, idiopathic Addison disease, idiopathic thrombo-cytopenic purpura, juvenile onset type diabetes, leukopenia, myasthenia gravis, paroxysmal cold hemoglobinuria, pernicious anemia, primary biliary cirrhosis, Sjögren syndrome, sympathetic ophthalmitis, systemic lupus erythematosus, and Wagener granulomatosis.

As described above, the agent exhibits anti-allergic effects. In addition, it can be daily used without affecting living bodies applied therewith. Therefore, since it efficiently enhances the anti-allergic effect in living bodies without causing serious side effects, it attains the prevention, early alleviation or treatment of allergic diseases and maintains healthy condition.

Recently, royal jelly has been reported to have an anti-allergic effect by Oka H. et al. ("*Biotherapy*", Vol. 14, pp. 145–150, (2000)) and Kataoka M. et al., ("*Natural Medicines*", Vol. 55, pp. 174–180, (2001)). However, such previous reports have not mentioned that a particular substance, selected from royal jelly ingredients such as proteins, saccharides, lipids, and others, is a main substance having anti-allergic activity. Therefore, the present invention firstly found the main substance to a protein having a partial amino acid sequence of SEQ ID NO: 1 or 2, and the royal jelly having a remarkable effect on inhibiting the production of cytokines, which can be confirmed by following Experiment 2, would exhibit a remarkable anti-atopic effect when orally administered as described in the following Experiment 7.

The following experiments explain the royal jelly or the anti-allergic protein used in the present invention in detail.

Experiment 1:

Preparation of Water-soluble Protein Fraction from Royal Jelly

Twenty-five grams of a refrigerated raw royal jelly from Brazil were thawed at room temperature, suspended in 20 mM Tris-HCl buffer (pH8.0) and dialyzed against five litters of the same buffer to remove low molecular substances from the royal jelly. The resulting dialysate was centrifuged (12,000 rpm, 15 minutes) to remove insoluble substances and filtrated with a 0.22-μm pore-sized filter to obtain a water-soluble protein fraction from royal jelly.

Experiment 2:

Measurement of Inhibition Activity for the Production of Cytokines or Cell Proliferation Using Mouse Spleen Cell Spleen cells were collected from BALB/c mouse immunized three times with OVA as an antigen and Alum as an adjuvant, and prepared to give concentration of $5 \times 10^6$ cell/ml. One hundred microliter aliquots of the resulting cell suspension were placed in a 96 wells microplate conjugated with anti-CD3 antibody (5 μg/ml). The raw royal jelly used in Experiment 1 or the water-soluble protein fraction obtained in Experiment 1 was diluted to concentration of 2.0 mg/ml or 4.0 mg/ml, and the dilute was added to each well by 50 μl. Further, 50 μl of the medium were added to each well to give total volume of 200 μl. After culturing for 40 hours, the resulting culture medium was collected and provided for measuring each cytokine, IL-2 or IL-4, by usual enzyme liquid immunosorbent assay (ELISA). As a control, phosphate buffer saline (hereinafter, it is abbreviated as "PBS(−)") was prepared instead of using the water-soluble protein fraction from royal jelly. The relative production of cytokine by the raw royal jelly or the water-soluble protein fraction from royal jelly was evaluated as percent value by comparing the each value of sample with the control value defined as 100%. The results are in Table 2.

TABLE 2

| Sample | Protein Concentration (mg/ml) | Relative Production of Cytokine (%) | |
|---|---|---|---|
| | | IL-2 | IL-4 |
| Control 1: PBS(−) | — | 100 | 100 |
| Control 2: Raw RJ | 2.0 | 103 | 73 |
| | 4.0 | 72 | 34 |
| Water-Soluble | 2.0 | 76 | 54 |

TABLE 2-continued

| Sample | Protein Concentration (mg/ml) | Relative Production of Cytokine (%) | |
| --- | --- | --- | --- |
| | | IL-2 | IL-4 |
| Protein Fraction from RJ | 4.0 | 43 | 16 |

"RJ": Royal Jelly,
"IL-2": Interleukin-2,
"IL-4": Interleukin-4

As shown in Table 2, the tested raw royal jelly and the water-soluble protein fraction from royal jelly inhibited the production of IL-2 or IL-4 dose-dependently. In the case of the raw royal jelly at the protein concentration of 2.0 mg/ml, the relative productions of IL-2 and IL-4 were 103% and 73%, respectively. In the case of the water-soluble protein fraction from royal jelly at the protein concentration of 2.0 mg/ml, the relative productions of IL-2 and IL-4 were 76% and 54%, respectively. These results revealed that the water-soluble protein fraction, which had been purified from royal jelly by removing non-protein substances such as water-soluble low molecular substances such as saccharide and water-insoluble substances using purification techniques such as dialysis and centrifuging, had higher inhibiting effect on the cytokine production (anti-allergic effect) than the raw royal jelly.

Experiment 3:

Purification of the Anti-allergic Proteins from Raw Royal Jelly and Physico-chemical Property of the Proteins Experiment 3-1:

Purification of the Anti-allergic Proteins from Raw Royal Jelly

Figure 2:
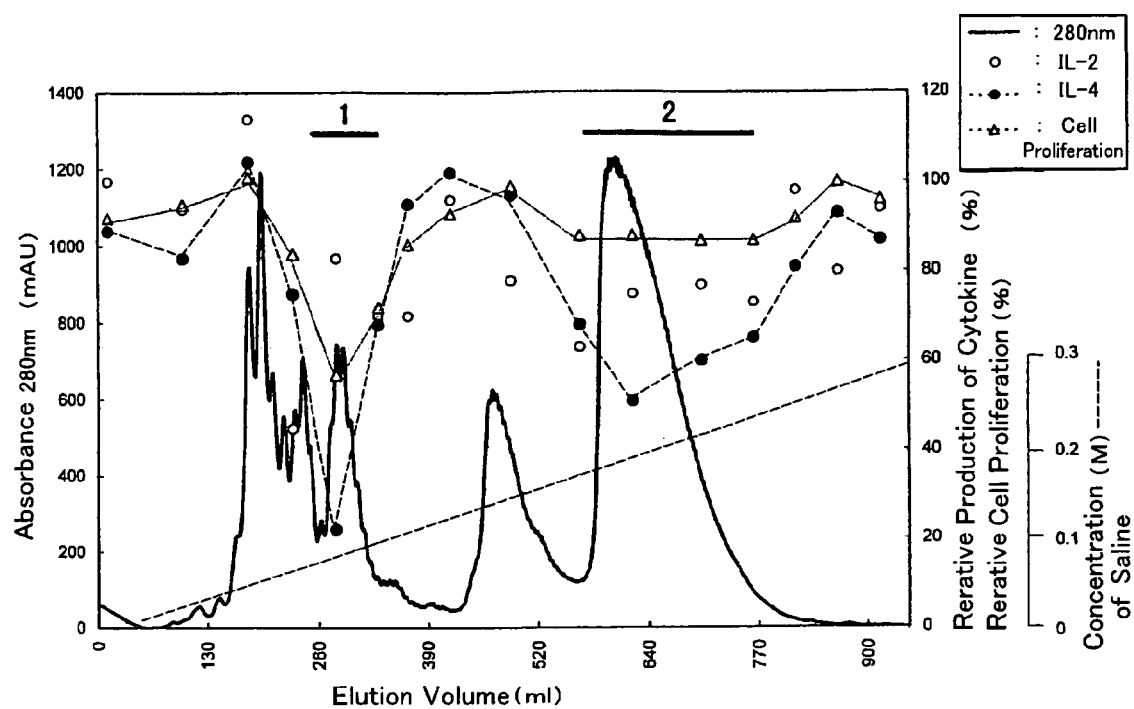
FIG. 2 is a chromatogram showing elution pattern of an active protein by applying a water-soluble protein fraction of royal jelly to an anion-exchange column chromatography using DEAE-5PW gel. (Open circles mean a relative production of IL-2; closed circles mean a relative production of IL-4; open triangles mean a relative cell proliferation rate, "No. 1" means an elute fraction of "Active Protein No. 1"; "No. 2" means an elute fraction of "Active Protein No. 2".)

Anti-allergic proteins were purified from a raw royal jelly as following up the inhibition of the cytokine production in spleen cells from mouse immunized with OVA/Alum according to Experiment 2. In addition, in order to calculate cell proliferation, the fluorescence intensity was measured by fluorometry using "Alamar Blue", a pigment as oxidation-reduction indicator commercialized by TREC DIAGNOSTIC Company in a manner of exciting with a wavelength of 544 nm wavelength and measuring with a wavelength of 590 nm. The water-soluble protein fraction obtained in Experiment 1 was applied to an anion-exchanger column chromatography (gel volume 54 ml) using "DEAE-5PW" gel commercialized by Tosoh Corporation, Tokyo, Japan. Since the proteins adsorbed to the gel had the inhibitory effect of the cytokine production and the cell proliferation they were eluted from the gel with sodium chloride solution in the manner of linear gradient of the concentration from 0 to 0.3 M. As a result, objective active proteins eluted at the concentration of about 0.08 M (represented by bold line 1 in FIG. 2) and at about 0.17 to 0.25 M (represented by bold line 2 in FIG. 2) were separately collected as chasing eluting protein by measuring 280 nm of absorbance. In the present invention, conveniently, the former protein is called as "Active Protein No. 1" and the later protein is called as "Active Protein No. 2". Followings are results of separately purifying the proteins.

Experiment 3-2:

Purification of "Active Protein No. 1"

Figure 3:
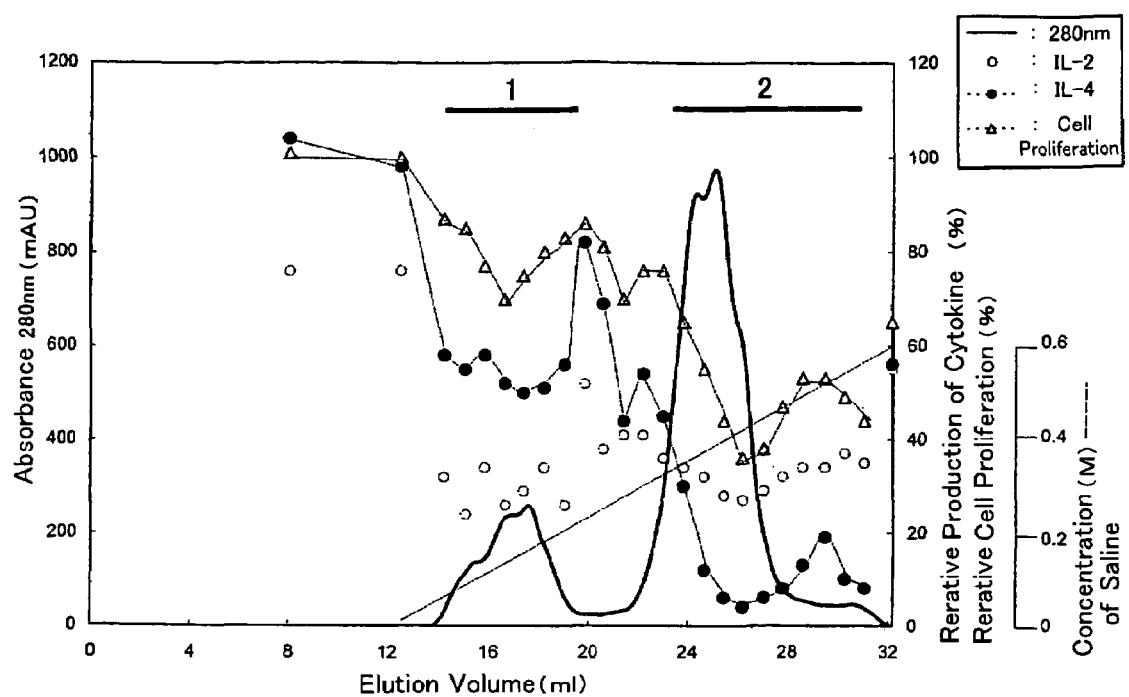
FIG. 3 is a chromatogram showing an elution pattern of an active protein by applying "Active Protein No. 1" to an affinity chromatography using Heparin-5PW gel. (Open circles mean relative production of IL-2; closed circles mean relative production of IL-4; open triangles mean relative cell proliferation rate, "No. 1" means elute fraction of "Active Protein No. 1-1"; "No. 2" means elute fraction of "Active Protein No. 1-2".)

The fraction containing "Active Protein No. 1" obtained in Experiment 3–1 was dialyzed against 20 mM Tris-HCl (pH8.0) solution containing 0.01 M sodium chloride. The resulting dialysate was applied to an anion-exchanger column chromatography (gel volume 6 ml) using "Resource Q" gel commercialized by Amersham Bioscience Corporation to be absorbed to the gel. The protein was eluted in active fractions near the sodium chloride concentration of 0.1 M in linear gradient from 0 to 0.5 M. The active fractions were collected and dialyzed against the same buffer containing 0.05 M sodium chloride to equilibrate with the buffer. The resulting dialysate was subjected to an affinity column chromatography using 3.3 ml of "Heparin-5PW" gel commercialized by Tosoh Corporation, Tokyo, Japan. The result is in FIG. 3. The "Active Protein No. 1" was allowed to adsorb to the gel and elute with saline in linear gradient of the concentration from 0 to 1M. Obtained each fraction was measured by the same method described in Experiments 2 and 3 to select the active fractions having the inhibitory effect of the cytokine production and the cell proliferation. As a result, two active proteins were obtained; an active protein eluted with about 0.15 M saline (represented by bold line 1 in FIG. 3, hereinafter, it is called as "Active Protein No. 1-1") and another with about 0.35 M saline (represented by bold line 2 in FIG. 3, hereinafter, it is called as "Active Protein No. 1-2"). Both proteins had the following same N-terminal amino acid sequence. The "Active Protein No. 1-2" was selected as a candidate to obtain a further purified active protein because the protein had larger molecular weight and higher specific activity than the "Active Protein No. 1-1". The fractions containing the "Active Protein No. 1-2" was subjected to gel filtration column chromatography using "Superdex 200" gel commercialized by Amersham Bioscience Corporation with 1.5 folds concentration of PBS (phosphate buffer saline). The purified "Active Protein No. 1" having the inhibitory effect on the production of cytokines and the cell proliferation was obtained by collecting the active fraction. Total protein and specific activity of the "Active Protein No. 1" at each purification step are in Table 3. In the Table 3, values of the active fraction of "DEAE-5PW" and below are of "Active Protein No. 1-2".

TABLE 3

| Step of Purification | Volume (ml) | Total Protein (mg) | Relative Production of IL-4 (%)* |
| --- | --- | --- | --- |
| Water Soluble Royal Jelly | 475 | 1057 | 9 |
| "DEAE-5PW" | 325 | 114 | 23 |
| "RESOURCE Q" | 40 | 80 | <2 |
| "Heparin-5PW" | 95 | 38 | 24 |
| "Superdex 200" | 20 | 30 | 6 |

*Values of the undiluted solution obtained from the step.

The obtained purified "Active Protein No. 1" specimen was subjected to SDS-PAGE using 10% (w/v) gel under a reducing condition with dithiothreitol (DTT) in order to determine the purity of the purified specimen. As a result, it had been observed a single band on SDS-PAGE and realized a highly purified specimen.

Experiment 3-3:

Physico-chemical Property of "Active Protein No. 1"

(1) Molecular Weight

The purified "Active Protein No. 1-2" having the effect of inhibiting the production of cytokines and cell proliferation against mouse spleen cell immunized with OVA/Alum prepared in Experiment 3-2 and the partially purified "Active Protein No. 1-1" prepared in Experiment 3-2, were subjected to SDS-PAGE under the reducing condition with DTT according to Experiment 3-2. The molecular weights of the proteins were calculated in comparison with "LMW Electrophoresis Calibration Kit", a molecular marker commercialized by Amersham Bioscience Corporation, simultaneously subjected to the SDS-PAGE with the proteins. As a result, "Active Protein No. 1-1" was detected as a protein band at the position of about 70 kDa and "Active Protein No. 1-2" was detected as a protein band at the position of about 55 kDa.

(2) N-terminal Amino Acid Sequences

N-terminal amino acid sequences of the both proteins prepared in Experiment 3-2, i.e., the purified "Active Protein No. 1-2" and partially purified "Active Protein No. 1-1", were analyzed with a usual protein sequencer (Model 473A, commercialized by Applied Biosystems). The both proteins had been determined to have N-terminal amino acid sequence at the position 1 to 10 of SEQ ID NO: 1. The "Active Protein No. 1-2" having about 70 kDa of molecular weight had been given the name "RJP70" by the present inventors.

Experiment 3-4:

Purification of "Active Protein 2"

The dialysate obtained by dialyzing the fraction containing "Active Protein No. 2" prepared in Experiment 3-1 against 20 mM Tris-HCl buffer (pH 8.0) containing 0.01 M saline was subjected to an anion exchange column chromatography using 6 ml gel volume of "Resource Q" gel commercialized by Amersham Bioscience Corporation. The "Active Protein No. 2" was adsorbed to the gel and eluted with saline in step gradient of the concentration from 0.1 to 0.4 M. The resulting active fractions containing "Active Protein No. 2" were collected, subjected to gel filtration column chromatography using "Superdex 200" gel (gel volume 320 ml, commercialized by Amersham Pharmacia Biotech Corporation) and eluted with 1.5 folds concentration of PBS(-). As a result, two active fractions were obtained. The fractions were supposed to separate due to difference of monomer and polymer in considering with a evidence of SDS-PAGE under reducing condition showing that the proteins of both fractions has the same molecular weight of 55 kDa. The both fractions were collected and obtained the purified "Active Protein No. 2" having inhibitory effect of cytokine production and cell proliferation against mouse spleen cell immunized with OVA/Alum. The results of total proteins and specific activities are in Table 4.

TABLE 4

| Step of Purification | Volume (ml) | Total Protein (mg) | Relative production of IL-4 (%)* |
|---|---|---|---|
| "DEAE-5PW" | 88 | 40.7 | 61.2 |
| "RESOURCE Q" | 2.8 | 36.3 | 22.8 |
| "Superdex 200" | 8.5 | 23 | 18.9 |

*Values of the undiluted solution obtained from the step.

The obtained purified "Active Protein No. 2" specimen was subjected to SDS-PAGE using 10% (w/v) gel under reducing condition with DTT in order to determine the purity of the purified specimen. As a result, it had been observed as a single band on SDS-PAGE to be a highly purified specimen.

Experiment 3-5:

Physico-chemical Property of "Active Protein No. 2"

(1) Molecular Weight

The purified "Active Protein No. 2" prepared in Experiment 3-4 was subjected to SDS-PAGE under reducing condition with DTT according to Experiment 3-3. As a result, "Active Protein No. 2" was detected as a protein band at the position of about 55 kDa.

(2) N-Terminal Amino Acid Sequences

N-terminal amino acid sequences of the purified "Active Protein No. 2" were analyzed with a usual protein sequencer (Model 473A, commercialized by Applied Biosystems). The protein had been determined to have N-terminal amino acid sequence at the position 1 to 25 of SEQ ID NO: 2. The "Active Protein No. 2" had been given the name "RJP55" by the present inventors.

Experiment 4:

Inhibitory Effect of the Purified "RJP70" Specimen on the Production of Cytokines The purified "RJP70" specimen prepared in Experiment 3-2 was serially diluted to give the solution at the concentrations of 11.7, 23.4, 46.9, 93.8, 188 and 375 µg/ml. The resulting solutions were examined about the inhibitory effect on the production of cytokines against mouse spleen. The activity on cell proliferation was also examined according to Experiment 3-1. The results are in Table 5.

TABLE 5

| | Relative Production of Cytokines and Cell Proliferation (%) | | |
|---|---|---|---|
| Sample | IL-2 | IL-4 | Cell Proliferation |
| Control (PBS(-)) | 100 | 100 | 100 |
| 11.7 µg/ml of the Purified "RJP70" Specimen | 78 | 93 | 96 |
| 23.4 µg/ml of the Purified "RJP70" Specimen | 84 | 105 | 100 |
| 46.9 µg/ml of the Purified "RJP70" Specimen | 62 | 57 | 83 |
| 93.8 µg/ml of the Purified "RJP70" Specimen | 70 | 41 | 68 |
| 188 µg/ml of the Purified "RJP70" Specimen | 63 | 33 | 68 |
| 375 µg/ml of the Purified "RJP70" Specimen | 42 | 8 | 49 |

IL-2: Interleukin-2,
IL-4: Interleukin-4

As shown in Table 5, the purified "RJP70" specimen was revealed to inhibit the production of IL-2 and IL-4 and cell proliferation dose-dependently.

Experiment 5:

Effects and Cytotoxity Against T Cell or Macrophage of the Purified "RJP70" Specimen Experiment 5-1:

Effects and Cytotoxity Against T Cell of the Purified "RJP70" Specimen

For the purpose of determining the direct effect and cytotoxity against T cell of the purified "RJP70" specimen, such activity of the specimen was measured by a test using $CD4^+$ T cell from mouse spleen cell stimulated with anti CD3 antibody. The spleen cell prepared from BALB/c mouse in Experiment 2 was suspended in RPM11640 medium supplemented with 10% (v/v) fetal calf serum (FCS). A cell sample containing CD4⁺ T cells was separated from the resulting cell suspension by the steps of; removing adhesive cells by keeping on dishes coated with FCS at 37° C. for one hour; removing B cells by keeping on dishes coated with goat anti mouse Ig, and; collecting CD4⁺ T cells by binding them to dishes coated with anti mouse CD4 antiserum. As a result, the obtained cell sample was occupied 91 to 93% by CD4⁺ T cells.

The inhibitory effect of the purified "RJP70" specimen prepared in Experiment 3-2 on the production of cytokines, i.e., IL-2, IL-4 and IFN-γ, was determined by a test using the CD4⁺ T cells and the specimens serially diluted to the concentration of 31.3, 62.5, 125 and 250 μg/ml. The relative value was calculated by comparing the purified "RJP70" specimen with a control treated in the same test except using PBS(−) instead of the purified "RJP70" specimen. The numbers of living cells or dead cells were measured by trypan blue dye exclusion method to calculate viability (%) according to the following numerous formula 1 as an indicator for cytotoxicity. The results are in Table 6.

Viability (%)={[the number of living cells]/([the number of living cells]+[the number of dead cells])}×100    Numerous Formula 1:

TABLE 6

| Sample | Relative Production of Cytokines (%) | | | Viability (%) |
| --- | --- | --- | --- | --- |
| | IL-2 | IL-4 | IFN-γ | |
| Control (PBS(−)) | 100 | 100 | 100 | 84.1 ± 2.4 |
| 31.3 μg/ml of the Purified "RJP70" Specimen | 78 | 97 | 96 | 83.8 ± 2.5 |
| 62.5 μg/ml of the Purified "RJP70" Specimen | 59 | 84 | 91 | 82.7 ± 1.9 |
| 125 μg/ml of the Purified "RJP70" Specimen | 24 | 68 | 68 | 84.6 ± 0.1 |
| 250 μg/ml of the Purified "RJP70" Specimen | 3 | 13 | 27 | 85.0 ± 1.5 |

As shown in Table 6, "RJP70" inhibited the production of IL-2, IL-4 and IFN-γ in the test using CD4⁺ T cells as well as using mouse spleen cells. "RJP70" was thought to have no cytotoxicity from the evidence of no significantly different viability between "RJP70" specimens and the control.

Experiment 5-2:

Effect and Cytotoxicity Against Macrophage of the Purified "RJP70" Specimen

To determine the direct effect and cytotoxicity against macrophage of "RJP70", this experiment that macrophage prepared from mouse abdomen was stimulated with lipopolysaccharide (LPS) and IFN-γ was carried out. BALB/c mouse was injected with 2 ml of 3% Brewer's thioglycollate medium. Ascites was taken from the mouse after three or four days and diluted with RPMI1640 medium supplemented with 10% (v/v) fetal calf serum to prepare the cell suspension at the concentration of $1 \times 10^6$ cells/ml. The cell suspension was placed in plastic dishes by 10 ml and incubated at 37° C. in 5% $CO_2$ for two hours. After discarding the medium, the dishes were washed twice with the fresh same medium to remove non-adhesive cells. Adhesive cells remaining the dishes were collected as macrophage preparation used in following experiment by suspending with the above medium using cell scraper. The inhibitory effect on the cytokine production was examined using the purified "RJP70" prepared in Experiment 3-2 and the macrophage preparation. In detail, the purified "RJP70" specimen was serially diluted to 150, 300 or 600 μg/ml and examined about the inhibitory effect on the production of TNF-α and IL-6. Relative values of the cytokine production were calculated by comparing with the control sample treated in the same manner using PBS(−) instead of the purified "RJP70" specimen. Viability of macrophage as a cytotoxicity was calculated by applying the numbers of living cell and dead cell counted by trypan blue dye exclusion method to the above numerous formula 1. The results are in Table 7.

TABLE 7

| Sample | Relative Production of Cytokines (%) | | Viability (%) |
| --- | --- | --- | --- |
| | TNF-α | IL-6 | |
| Control (PBS(−)) | 100 | 100 | 100 |
| 150 μg/ml of the Purified "RJP70" Specimen | 85 | 103 | 96 |
| 300 μg/ml of the Purified "RJP70" Specimen | 74 | 98 | 92 |
| 600 μg/ml of the Purified "RJP70" Specimen | 28 | 99 | 100 |

As shown in Table 7, "RJP70" was revealed to inhibit the production of TNF-α in the test using macrophage with LPS and IFN-γ but not the production of IL-6, and have no cytotoxicity from the evidence of no significantly different viability between "RJP70" specimens and the control.

Experiment 6:

Effect of Royal Jelly and the Purified "RJP70" Specimen on Inhibiting the Production of Antibodies It was examined how an administration of royal jelly or "RPJ70" influenced to the antibody production in a mouse immunized with OVA/Alum. Five of seven weeks-aged female BALB/c mice (commercialized by Charles liver Japan, Inc., Kanagawa, Japan) were divided in one group and intraperitoneally immunized three times with 2 μg of OVA and 3 mg of Alum in one week-interval. Royal jelly was the same one used in Experiment 1 and it was dissolved in PBS(−) and applied to mouse by 50 μg per one shot. "RJP70" was prepared in Experiment 3-2 and it was dissolved in PBS(−) and applied to mouse by 0.5, 5 or 50 μg per one shot. Each sample was intraperitoneally applied to the mouse twice; two days and six hours before each the three times of the immunization with OVA/Alum, and totally applied six times. As a control, PBS(−) was applied in the same manner. The results of test group are summarized in Table 8.

TABLE 8

| Group | Sample | Dose/Times | Number of Mouse | Method of Immunizing (Induction of IgE) |
| --- | --- | --- | --- | --- |
| 1 | PBS(−) (Control 1) | — | 5 | OVA/Alum 3 times Intraperitoneal |
| 2 | Royal Jelly (Control 2) | 50 μg/mouse 6 times | 5 | OVA/Alum 3 times Intraperitoneal |
| 3 | "RJP70" | 50 μg/mouse 6 times | 5 | OVA/Alum 3 times Intraperitoneal |
| 4 | "RJP70" | 5 μg/mouse 6 times | 5 | OVA/Alum 3 times Intraperitoneal |
| 5 | "RJP70" | 0.5 μg/mouse 6 times | 5 | OVA/Alum 3 times Intraperitoneal |

OVA: egg albumin (antigen)
Alum: aluminium hydrate gel (adjuvant)

The serum samples were taken from mice after one week from the third immunization. Levels of various antibodies in each serum sample was measured by enzyme immunoassay (EIA) method. Titer of anti-OVA IgE antibody was calculated by calibrating the values measured by captured EIA method with the standard curve made by standard serum (640 U/ml). Each calculated value was analyzed in a manner of comparing test groups with control group, i.e., statistical t-test or Welch test, whether it was significant. Significantly different values in one group were dismissed by applying Smirnov outlier test. The result of anti-OVA IgE antibody was in FIG. 4 while the result of anti-OVA IgGi antibody was in FIG. 5.

Figure 4:
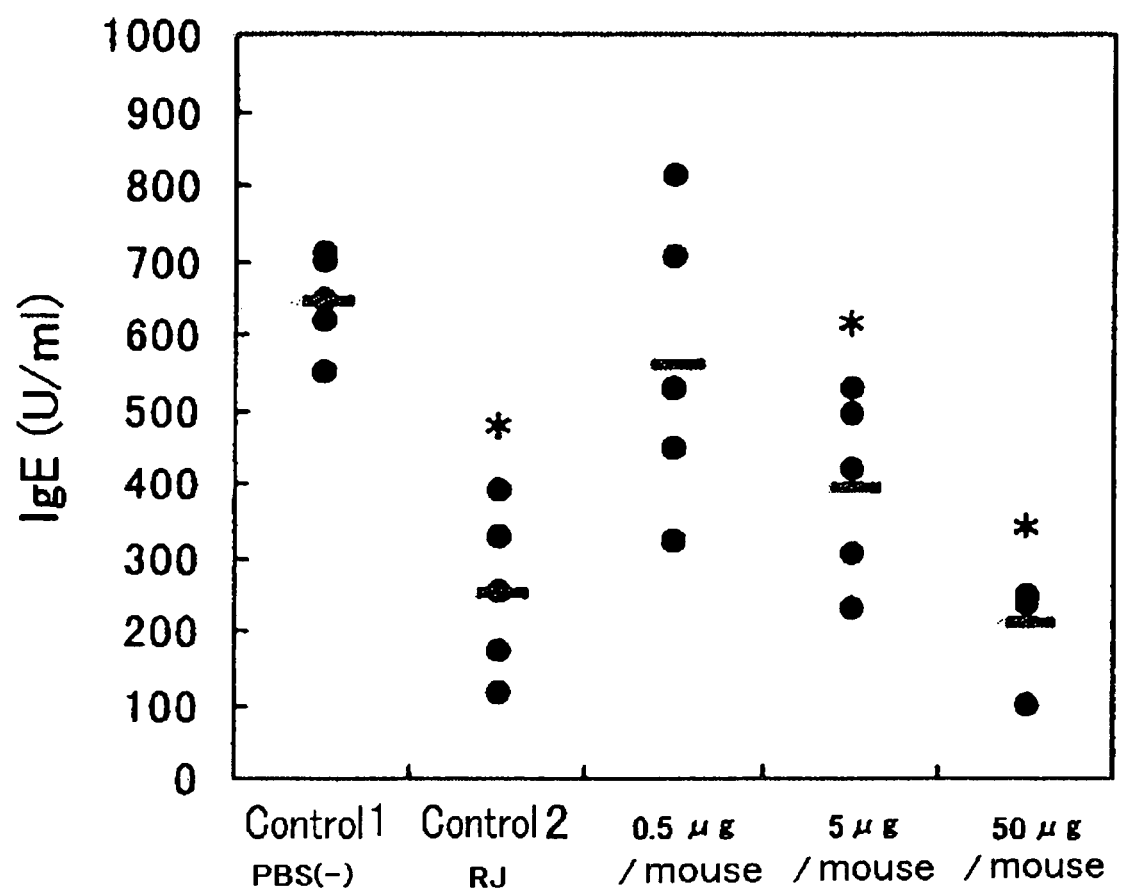
FIG. 4 shows a result of measuring anti-OVA IgE antibody value in serum of OVA/Alum immunized male BALB/c mouse when intraperitoneally administered with royal jelly or "RJP70".

As shown in FIG. 4, both of royal jelly and "RJP70" were revealed to have the effect on decreasing the titer of anti-OVA IgE antibody. Royal jelly was demonstrated to significantly decrease the titer of anti-OVA IgE antibody down to 61% of control (PBS(−)). The purified "RJP70" specimen was demonstrated to dose-dependently decrease the titer of anti-OVA IgE, concretely, the decreasing rate of the group administered with 0.5 μg/mouse was 13%, 5 μg/mouse was 39%, and 50 μg/mouse was 67%. As shown in FIG. 5, the groups administered with royal jelly or the purified "RJP70" specimen were observed to significantly decrease the titer of anti-OVA IgG1 antibody down to 46–82% of the control as well as that of anti-OVA IgE antibody.

It was determined by the above results that royal jelly and "RJP70" used in the present invention had the inhibitory effect on allergy reaction from the evidence that they decreased the production of IgE and IgG1 antibody.

Experiment 7:

Inhibitory Effect on Atopic Dermatitis

Inhibitory effect on atopic dermatitis of the raw royal jelly used in Experiment 1 and "RJP70" prepared in Experiment 3-2 was examined using "atopic dermatitis model mouse" which was an Nc/Nga mouse (female, five weeks-aged, commercialized by Charles liver Japan, Inc., Kanagawa, Japan) induced into dermatitis similar to atopic dermatitis by applying picryl chloride. In detail, the five weeks-aged Nc/Nga mouse was first sensitized by; applying ethanol/acetone mixture (4:1 by volume) containing 5% (w/v) picryl chloride on its abdomen and breast shaved with hair clippers; after four days, applying olive oil containing 1% (w/v) picryl chloride on its back and earlobes in the anesthetized condition; applying the olive oil every other week five times. While 1.0 mg of the raw royal jelly used in Experiment 1 or 0.3 mg of the purified "RJP70" specimen prepared in Experiment 3-2 was orally applied to 10 of the mice by sonde once a day five times a week for six weeks from three days before the first sensitization. Skin condition such as itch, redness, bleeding, edema, abrasion, tissue deficit, formation of crust and dryness was megascopically judged twice a week from three weeks after the first sensitization.

Since mice of the group applied with raw royal jelly and "RJP70" had significantly better condition than mice of control group, raw royal jelly and "RJP70" inhibited the symptoms of atopic disease. The result shows that royal jelly and anti-allergic protein "RJP70" used in the present invention are a substance having the effect on alleviating atopic allergic symptoms.

Experiment 8:

Acute Toxicity Test

An appropriate amount of "RJP70" or "RJP55" was dissolved in physiological saline containing 5% by weight of gum Arabic and sterilized by usual filtration. Ten ddY mice weighing 20–25 g were administered with the resulting solution by intraperitoneal injection or oral intake using a sonde, and observed for seven days. As a result, when the maximum dose was 10 mg/kg body weight, no fatal case was observed in all groups. The results verify that anti-allergic protein "RJP70" and "RJP55" used in the present invention are safe substances enable to regular use.

Experiment 9:

Cloning DNA (cDNA) Encoding "RJP70" and "RJP55"

Experiment 9-1:

Preparation of Total RNA from Honeybee

Total RNA preparation was carried out using "TOTALLY RNA KIT", an RNA preparation kit commercialized by Ambion Inc., availing usual guanidinthiocyanate/acidic phenol: chloroform method according to the attached protocol. Twelve heads of imaginal *Apis mellifera* L. were immersed in "denaturalized solution" and homogenized. With 10 ml of the obtained extraction was admixed equal volume of phenol: chloroform: isoamylalcohol (25:24:1 by volume). After centrifuging, upper layer was collected, then, mixed with 0.1 volume of 3 M sodium acetate solution (pH 4.5) and following equal volume of acidic phenol: chloroform solution. After centrifuging, upper phase was collected and mixed with isopropanol. The resulting solution was kept at −20° C. for one hour and centrifuged. The resulting precipitate was washed with 70% (v/v) ethanol solution, dried and dissolved in 300 μl of 0.1 mM ethylendiaminetetraacetic acid (EDTA) solution. The resulting solution was heated at 70° C. for 10 minutes, admixed with 150 ml of 7.5 M lithium chloride and 50 mM EDTA, kept at −20° C. for one hour and centrifuged. The resulting precipitate was washed with 70% (v/v) ethanol aqueous solution, dried, and dissolved in diethylpyrocarbonate (DEPC) treated water containing 0.5 mM EDTA. Finally, 186 μg of total RNA preparation was obtained.

Experiment 9-2:

Cloning of cDNA Encoding "RJP70"

Five microliter of 1 μg/μl total RNA prepared in Experiment 9-1 was placed into 0.5-ml volume tube and admixed with 5 μl of 0.2 μg/μl random hexanucleotide primer and 50 μl of DEPC treated water. The tube was set on "DNA Thermal Cycler 480" a thermal cycler commercialized by PerkinElmer Inc., heated at 70° C. for five minutes and quickly cooled down at 4° C. Then, 20 μl of 5 fold concentration of RT-PCR reaction mixture, 10 μl of 100 mM dithiothreitol, 5 μl of 25 mM dNTP, and 5 μl of 200 U/μl Moloney murine leukemia virus (M-MLV) reverse transcriptase (commercialized by Invitrogen Corporation) were added to the solution. The resulting reaction mixture was kept at 25° C. for 10 minutes, 40° C. for 30 minutes, and 99° C. for 5 minutes to obtain first strand cDNA solution through a reaction of reverse transcription. The resulting cDNA was subjected to usual PCR amplification using the synthetic oligonucleotide primers having the nucleotide sequence of SEQ ID NO: 9 as a sense primer and SEQ ID NO: 10 as an antisense primer which were referred to a nucleotide sequence of "MRJP3" disclosed in GenBank database. In detail, 2 μl of the reverse transcriptase product were admixed with 5 μl of 10 fold concentration "ExTaq" reaction mixture, 1 μl of 2.5 U/μl "ExTaq" polymerase, 4 μl of 2.5 mM dNTP, 1 μl of 100 ng/μl sense primer described above, 1 μl of 100 ng/μl antisense primer described above, and sterilized water up to 50 μl of total volume. The reaction mixture was subjected to PCR reaction (35 cycles, at 94° C. for 30 seconds, at 61° C. for 30 seconds and 72° C. for three minutes). When the resulting PCR product was subjected to 0.9% agarose gel electrophoresis, amplified DNA fragments were detected as about 1,600 bp-DNA band. The DNA fragments were collected from the gel by usual extraction method. An aliquot of the obtained DNA was subjected to ligation reaction using "pCR-Script SK(+) Cloning Kit" with plasmid vector "pCR-Script Cam SK (+)" according to an attached protocol. An aliquot of the reaction mixture was introduced into "XL10-Gold Kan" an E. coli competent cell commercialized by Stratagene to make a transformed E. coli according attached protocol. The transformed E. coli was placed on LB agar plate (1% sodium chloride, 1% tryptone, 0.5% yeast extract, 2% agar) containing 30 μg/ml chloramphenicol and incubated at 37° C. for 16 hours. E. coli was picked up from the appearing colony and incubated in LB liquid medium containing 30 μg/ml chloramphenicol at 37° C. for 16 hours by shaking. Recombinant DNA was prepared from the resulting E. coli by usual method. The recombinant DNA was subjected to sequence analysis according to usual "dideoxy" method using a DNA sequencer model "373A" commercialized by Applied Biosystems, and had the nucleotide sequence of SEQ ID NO: 5 as "RJP70" cDNA. The amino acid sequence of SEQ ID NO: 3 is a mature type protein without 20 amino acid residues corresponding to secretion signal sequence from the amino acid sequence encoded by the nucleotide sequence of SEQ ID NO: 5.

Experiment 9-3:

Cloning cDNA Encoding "RJP55"

A cDNA encoding "RJP55" was cloned and sequenced by the same manner described in Experiment 9-2 except for using PCR primers having the nucleotide sequence of SEQ ID NO: 11 as a sense primer and SEQ ID NO: 12 as an antisense primer selected from the nucleotide sequence of "MRJP1" disclosed in GenBank database and setting PCR reaction condition 35 cycles at 94° C. for 30 seconds, at 46° C. for 30 seconds, at 72° C. for three minutes. The cloned "RJP55" cDNA had the nucleotide sequence of SEQ ID NO: 6. The amino acid sequence of SEQ ID NO: 4 is a mature type protein without one amino acid residue of methionine encoded by start codon "ATG" corresponding to secretion signal sequence from the amino acid sequence encoded by the nucleotide sequence of SEQ ID NO: 6.

Experiment 10:

Production of Anti-allergic Protein By Recombinant DNA Technique

Experiment 10-1:

Preparation of a Baculovirus Transformed with "RJP70" cDNA

Baculovirus for expressing the recombinant protein in insect cell was prepared using "BD BaculoGold Transfection Kit" commercialized by BD Pharmingen Corporation. The recombinant DNA prepared in Experiment 9-2 was digested with restriction enzyme Not I and BamH I. The resultant was subjected to 0.9% (w/v) agarose electrophoresis and the DNA fragment at about 1,600 bp was extracted from the gel and purified. The obtained DNA fragment was ligated to baculovirus transfer vector "pVL1393" at BamH I—Not I recognition site down from polyhedorin promoter using "Ligation Kit Version 2" commercialized by Takara Shuzo Corporation, Kyoto, Japan. An aliquot of the ligation reaction was introduced into "Competent Cell JM109" commercialized by Takara Shuzo Corporation, Kyoto, Japan, to make transformed E. coli according to attached protocol. The transformed E. coli was placed on an LB agar (2%) plate containing 40 μg/ml ampicillin and incubated at 37° C. for 16 hours. The transformed E. coli was picked up from an appeared colony and incubated in LB liquid medium containing 40 μg/ml ampicillin at 37° C. for 16 hours by shaking. The recombinant DNA was prepared from the E. coli, and then, the insertion of "RJP70" cDNA was confirmed. The obtained "RJP70" recombinant vector was named as "pVL1393-rip70-4". Recombinant virus was prepared using Sf9 insect cell (ATCC CRL-1711, fall armyworm) according to attached protocol. The Sf9 cell was placed in six-well plate with TC100 medium supplemented with 10% (v/v) FCS (commercialized by Invitrogen Corporation) and kept for 10 minutes to attach the plate bottom. After removing the supernatant, 0.5 ml of "Transfection Buffer A Solution" (Grace's medium containing 10% (v/v) FCS) was thrown into each well. While 1.5 μg of the "pVL1393-rjp70-4" and 0.25 μg of "BD Baculovirus DNA" were admixed and incubated for five minutes. To the resultant was added 0.5 ml of "Transfection Buffer B" (125 mM calcium chloride, 140 mM sodium chloride, 25 mM HEPES (pH7.1)). Then 0.5 ml of the resulting solution was thrown into the each well and incubated at 27° C. for four hours for infection reaction. As a control, "Buffer B" containing wild type baculovirus was added and infected to Sf9 insect cell in the same manner. The resulting virus solution was amplified by adding 50 to 200 μl of the solution to $1 \times 10^7$ cells of Sf9 cell and incubating it at 27° C. for one week. The resulting culture supernatant was prepared as recombinant virus solution for expression of "RJP70" and virus control solution (wild type virus) by centrifuging.

Experiment 10-2:

Preparation of "RJP70" Recombinant Protein

"High Five", an insect cell line from Trichoplusia ni (commercialized by Invitrogen Corporation) was used as a host cell for the protein expression. Virus infection was carried out by adding 200 μl of recombinant virus of "RJP70" solution to 10 ml of $1 \times 10^8$ Sf9 cell suspension with "Express Five Non-Serum Medium" commercialized by Invitrogen Corporation and incubating for one hour as mixing every 10 minutes. The resulting solution was admixed with 40 ml of the "Express Five Non-Serum Medium" and incubated at 27° C. for one week. The resulting culture supernatant was centrifuged by 15,000 rpm for 30 minutes to remove virus and concentrated by centrifuging with "Ultrafree15 UFV2BTK10<30000" a limit filtration membrane for under 30 kDa commercialized by Millipore Corporation. The resulting solution was subjected to "PD-10" a gel column packing "Sephadex G-25M" (commercialized by Amersham Bioscience Corporation) to obtain a recombinant "RJP70" solution dissolved in 1.5 fold concentration of PBS(−). The obtained solution was a 20 fold concentrated solution of the starting solution and usable for the following assay. A control solution was prepared in the same manner except of using the virus control solution instead of the "RJP70" recombinant virus solution.

Experiment 10-3:

Effect of the Recombinant "RJP70" on the Production of Cytokines

The inhibitory effect on the production of IL-2 and IL-4 of the recombinant "RJP70" was examined according to the method described in Experiment 2. In detail, the recombinant "RJP70" solution prepared in Experiment 10-2 or the control solution was diluted with 0.5 volume sterilized water. The activities of the resultant were measured. Then, the activity of "RJP70" on the production of cytokines was judgement by calculating relative values comparing with that of control as 100%. The results are in Table 8.

TABLE 8

| Sample | Relative Production of Cytokines (%) | |
|---|---|---|
| | IL-2 | IL-4 |
| Control (Virus Control) | 100 | 100 |
| 20 μg/ml of the Recombinant "RJP70"* | 101 | 86 |
| 102 μg/ml of the Recombinant "RJP70"* | 60 | 79 |
| 307 μg/ml of the Recombinant "RJP70"* | 57 | 66 |
| 920 μg/ml of the Recombinant "RJP70"* | 43 | 49 |

*The values mean a total protein concentration in the supernatant of the virus-infected cell culture.

As shown in Table 8, recombinant "RJP70" solution inhibited the production of IL-2 and IL-4 dose-dependently. The result was revealed that "RJP70" protein had an anti-allergic effect.

The following Examples concretely explain the present invention in detail. The present invention is not restricted to the Examples.

EXAMPLE 1

Anti-allergic Agent

The purified "RJP70" specimen prepared in Experiment 3-2 and determined physico-chemically in Experiment 3-2 was freeze-dried in vacuo. One point five parts by weight of the resultant were homogenously admixed with 8.5 parts by weight of "TREHA®", a crystalline hydrous α,α-trehalose commercialized by Hayashibara Shoji, Inc., Okayama, Japan, and powdered by pulverizer. The resulting powder was passed though a 0.42-mm mesh to prepare the anti-allergic agent of the present invention. The anti-allergic agent was confirmed to have the anti-allergic effect on inhibiting the production of cytokines by testing the effect according to Experiment 2. Further, it was reconfirmed by the same test after 10 days.

The anti-allergic agent was provided to produce a tablet weighing 200 mg by tablet machine. The product is a conveniently usable anti-allergic agent exhibiting a remarkable and stable anti-allergic effect even after preservation at normal temperature. The product is useful as a health food in daily use because of its mellow sweet taste.

EXAMPLE 2

Anti-allergic Agent

The anti-allergic agent of the present invention was prepared by mixing following ingredients homogeneously in the manner according to Example 1. As "RJP70" and "RJP55" described below, the purified specimens prepared in Experiment 3-2 and 3-4 and physico-chemically determined in Experiment 3-3 and 3-5 were added after freeze-dried in vacuo and weighed. The prepared agent was confirmed to have the stable anti-allergic effect even after preservation at normal temperature according to Experiment 2.

| | |
|---|---|
| "TREHA ®" (an α,α-trehalose commercialized by Hayashibara Shoji Inc., Okayama, Japan) | 7.7 parts by weight |

-continued

| | |
|---|---|
| Freeze-dried powder of the purified "RJP70" specimen | 1.0 part by weight |
| Freeze-dried powder of the purified "RJP55" specimen | 0.4 parts by weight |
| "αG HESPERIDIN PS" (a saccharide-transferred hesperidin commercialized by Hayashibara Shoji Inc., Okayama, Japan) | 4 parts by weight |
| "PULLAN PF-20" (a pullulan commercialized by Hayashibara Shoji Inc., Okayama, Japan) | 0.5 parts by weight |

The anti-allergic agent was provided to produce a tablet weighing about 300 mg by tablet machine. The product is a conveniently usable anti-allergic agent exhibiting a remarkable and stable anti-allergic effect even after preservation at normal temperature. The product is useful as a health food in daily use because of its mellow sweet taste.

EXAMPLE 3

Anti-allergic Agent

The anti-allergic agent of the present invention was prepared by mixing following ingredients homogeneously in the manner according to Example 1. As a partial purified royal jelly described below, "Active Protein No. 1" purified partially by an anion column chromatography using "DEAE-5PW" gel commercialized by Tosoh Corporation, Tokyo, Japan were added after freeze-dried and weighed. The prepared agent was confirmed to have the stable anti-allergic effect even after preservation at normal temperature according to Experiment 2.

| | |
|---|---|
| "FINETOSE ®" (crystalline anhydrous maltose commercialized by Hayashibara Shoji Inc., Okayama, Japan) | 7.5 parts by weight |
| Freeze-dried powder of the partial purified royal jelly | 1.5 parts by weight |
| Maltitol | 0.8 parts by weight |
| L-tryptophan | 0.2 parts by weight |

The product is a conveniently usable anti-allergic agent exhibiting a remarkable and stable anti-allergic effect even after preservation at normal temperature. The product is useful as a health food in daily use because of its mellow sweet taste.

EXAMPLE 4

Health Beverage

A composition containing 500 parts by weight of "FINETOSE®" a crystalline anhydrous maltose commercialized by Hayashibara Shoji Inc., Okayama, Japan, 100 parts by weight of the anti-allergic agent prepared in Example 3, 190 parts by weight of powered egg yolk, 200 parts by weight of skim milk, 4.4 parts by weight of sodium chloride, 1.85 parts by weight of potassium chloride, 4 parts by weight of magnesium sulfate, 0.01 part by weight of thiamin, 0.1 part by weight of sodium ascorbate, 0.6 parts by weight of vitamin E acetate, and 0.04 parts by weight of nicotinamide was prepared. Twenty-five parts by weight of the composition were dispersed and dissolved homogeneously in 150 parts by weight of purified water and placed in brown glass bottle by 150 g and sealed.

The product exhibits stable anti-allergic effect and is supplemented with nutrient sources, and can be advantageously used as a health beverage to keep health, promote growth, or prevent, alleviate and treat allergic symptoms. The product can also be used a composition in oral use or intubation use for animals such as domestic animals as well as humans.

EXAMPLE 5

Chewing Gum

Three parts by weight of heat-softened gum base, two parts by weight of "Crystalline MABIT" a crystalline anhydrous maltitol commercialized by Hayashibara Shoji Inc., Okayama, Japan, two parts by weight of xylitol, and four parts by weight of the anti-allergic agent prepared in Example 2 were admixed together and further mixed with proper amount of a flavor and colorant. The resultant was admixed with 0.5 parts by weight of "RJP70" prepared in Experiment 3-2 as kneeled by roller in a usual manner, and further kneeled, shaped, and packed to obtain a product.

Since the product has satisfactory texture, taste and flavor as well as an anti-allergic effect, it can be advantageously used as daily used chewing gum.

EXAMPLE 6

Skin External Cream

Following ingredients were admixed together as heated in a usual manner;

| | |
|---|---|
| Polyoxyethylene glyceryl monostearate | 2.0 parts by weight |
| Glyceryl monostearate, selfemulsifying | 5.0 parts by weight |
| Eikosanyl beheniate | 1.0 part by weight |
| Petrolatum | 1.9 parts by weight |
| Trioctanic trimethyrol propan | 10.0 parts by weight. |

The resulting mixture was admixed with following ingredients except the anti-allergic agent. After cooled down below 30° C., the mixture was admixed with the anti-allergic agent and emulsified by homogenizer to produce skin external cream.

| | |
|---|---|
| 1,3-butyleneglycol | 5.0 parts by weight |
| Sodium lactate (solution) | 10.0 parts by weight |
| Methyl parahydroxybenzoate | 0.1 part by weight |
| Peach leaf extract | 1.5 parts by weight |
| Purified water | 62.2 parts by weight |
| The anti-allergic agent powder prepared in Example 1 | 1.0 part by weight |

Since the cream has satisfactory moisture retention property and alleviates allergic symptom such as atopic dermatitis, it is useful as a skin external cream.

EXAMPLE 7

Liquid Preparation

The purified "RJP70" specimen purified in Experiment 3-2 and then physico-chemically determined in Experiment 3-3 was dissolved in physiological saline to give concentration of 0.1% by weight. The resulting solution was precisely filtrated to obtain a liquid preparation.

The product is useful for injection, eye drop, or nose drop to alleviate or treat allergic diseases such as polliosis.

EXAMPLE 8

Troche

Following ingredients were admixed together and treated according to Example 1 to produce the anti-allergic agent of the present invention in a powder form. The powdery agent was confirmed to have stable anti-allergic effect from a result that it inhibited the cytokine production even after preservation by the test according to Experiment 2.

| | |
|---|---|
| "FINETOSE ®" crystalline anhydrous maltose commercialized by Hayashibara Shoji, Inc., Okayama, Japan | 30 parts by weight |
| Starch | 30 parts by weight |
| The freeze-dried powder of the purified "RJP70" specimen prepared in Experiment 3-2 | 10 parts by weight |
| Crystalline cellulose | 19 parts by weight |
| Hydroxypropyl methyl cellulose | 10 parts by weight |
| Magnesium stearate | 1 part by weight |

A troche weighing about 1.0 g sized with 16 mm in diameter and 4 mm in thickness was produced from the anti-allergic agent by tablet machine. The product is a convenient and effective troche exhibiting anti-allergic effect even after preservation at a normal temperature. Since the product has mellow sweetness, it can be advantageously used as daily used troche for oral use to prevent atopic allergy, alleviate the symptom or promote treatment.

EXAMPLE 9

Tablet

Nine parts by weight of "FINETOSE®" a crystalline anhydrous maltose commercialized by Hayashibara Shoji, Inc., Okayama, Japan, and one part by weight of raw royal jelly (from Brazil) confirmed to have a high level of the inhibition of the cytokine production according to Experiment 2 were admixed together homogeneously. The mixture was kept at 25° C. for one night and powdered by pulverizer. The powder was passed through a 0.42-mm mesh in diameter and collect to obtain the powdery anti-allergic agent of the present invention.

The powdery agent was formed in a tablet weighing about 300 mg by tablet machine. The product is a convenient and effective anti-allergic agent exhibiting even after preservation at normal temperature. Since the product has mellow sweetness, it can be advantageously used as daily used anti-atopic agent for oral use to prevent atopic allergy, alleviate the symptom or promote treatment.

INDUSTRIAL APPLICABILITY

As described above, the present invention is to develop an anti-allergic agent comprising a protein having anti-allergic effect; or royal jelly or a purified royal jelly containing the protein based on a new finding that the protein obtainable form royal jelly or purified royal jelly, or royal jelly or purified royal jelly containing the protein exhibits an anti-allergic effect due to remarkably inhibiting the production of antibody or cytokine for mammals including human. Since the anti-allergic agent of the present invention is not need to concern a serious side effect, it is conveniently and comfortably used for preventing, alleviating and treating various symptoms caused by allergic diseases illustrated with atopic diseases and autoimmune disease against mammals including human. It can also be advantageously used in a form of food, beverage, cosmetic, or pharmaceutical.

Thus, the present invention has a remarkable effect and will give great contribution to the art.

---

The invention claimed is:

1. A purified anti-allergic royal jelly protein comprising an amino acid sequence of SEQ ID NO:3.

2. A food or beverage, which comprises the anti-allergic royal jelly protein of claim 1.

3. A cosmetic, which comprises the anti-allergic royal jelly protein of claim 1.

4. A pharmaceutical, which comprises the anti-allergic royal jelly protein of claim 1.

5. A method for treating or preventing allergic diseases, comprising administering to a patient in need thereof an effective amount of anti-allergic royal jelly protein,
 wherein said anti-allergic royal jelly protein comprises the amino acid sequence of SEQ ID NO:1 at the N-terminus and has a molecular weight of about 70 kDa on SDS-PAGE, and
 wherein said royal jelly anti-allergic protein comprises the amino acid sequence of SEQ ID NO: 3.

* * * * *